US008216282B2

(12) United States Patent
Hua

(10) Patent No.: US 8,216,282 B2
(45) Date of Patent: Jul. 10, 2012

(54) SYSTEM AND METHOD FOR WIRE-GUIDED PEDICLE SCREW STABILIZATION OF SPINAL VERTEBRAE

(76) Inventor: Sherwin Hua, Newhall, CA (US)

(*) Notice: Subject to any disclaimer, the term of this patent is extended or adjusted under 35 U.S.C. 154(b) by 0 days.

(21) Appl. No.: 13/246,432

(22) Filed: Sep. 27, 2011

(65) Prior Publication Data
US 2012/0016423 A1    Jan. 19, 2012

Related U.S. Application Data

(63) Continuation of application No. 13/122,388, filed as application No. PCT/US2009/059004 on Sep. 30, 2009.

(60) Provisional application No. 61/101,932, filed on Oct. 1, 2008.

(51) Int. Cl.
*A61B 17/70* (2006.01)
*A61B 17/86* (2006.01)

(52) U.S. Cl. ........................................ 606/264; 606/305

(58) Field of Classification Search .......... 606/246–256, 606/264–267, 278, 99, 96, 86 A, 190, 914, 606/104; 600/201, 203, 210
See application file for complete search history.

(56) References Cited

U.S. PATENT DOCUMENTS

| | | | |
|---|---|---|---|
| 4,448,191 A | 5/1984 | Rodnyansky et al. | |
| 5,092,866 A | 3/1992 | Breard et al. | |
| 5,242,443 A | 9/1993 | Kambin | |
| 5,306,275 A | 4/1994 | Bryan | |
| 5,672,175 A | 9/1997 | Martin | |
| 5,728,097 A | 3/1998 | Mathews | |
| 5,980,521 A | 11/1999 | Montague et al. | |
| 6,235,028 B1 | 5/2001 | Brumfield et al. | |
| 6,485,491 B1 | 11/2002 | Farris et al. | |
| 6,530,929 B1 | 3/2003 | Justis et al. | |
| 6,793,656 B1 | 9/2004 | Mathews | |
| 6,916,320 B2 | 7/2005 | Michelson | |
| 6,929,606 B2 | 8/2005 | Ritland | |
| 7,008,422 B2 | 3/2006 | Foley et al. | |

(Continued)

FOREIGN PATENT DOCUMENTS
WO    WO 2008/039247 A2    4/2008
(Continued)

OTHER PUBLICATIONS

U.S. Appl. No. 13/098,325, filed Apr. 29, 2011, Hua.
(Continued)

*Primary Examiner* — Pedro Philogene
(74) *Attorney, Agent, or Firm* — Knobbe Martens Olson & Bear LLP

(57) ABSTRACT

An improved system and method for positioning screws and rods to immobilize bones is provided. Specifically, the system and method is optimal for performing transforaminal lumbar interbody fusion (TLIF) and other interbody fusions in the spine. The system involves pedicle screws detachably connected to wires that guide rods down to the screws. The wires are strong, narrow, flexible, adjustable in tension, and easily disconnected from the screws after rod placement via a process such as cutting, radiating, burning, dissolving, etc. The use of wires to place the rods avoids the conventional bulky tower apparatuses of the prior art while at the same time enhancing the accuracy of placement. One of the preferred methods involves relying upon the natural lordotic curvature of the spine and the narrow diameter of the wires to insert many elements through a single minimally invasive incision.

30 Claims, 19 Drawing Sheets

U.S. PATENT DOCUMENTS

| | | | |
|---|---|---|---|
| 7,011,660 B2 | 3/2006 | Sherman et al. | |
| 7,063,725 B2 | 6/2006 | Foley | |
| 7,066,961 B2 | 6/2006 | Michelson | |
| 7,083,621 B2 | 8/2006 | Shaolian et al. | |
| 7,179,225 B2 | 2/2007 | Shluzs et al. | |
| 7,179,261 B2 | 2/2007 | Seivol et al. | |
| 7,188,626 B2 | 3/2007 | Foley et al. | |
| 7,250,052 B2 | 7/2007 | Landry et al. | |
| 7,282,064 B2 | 10/2007 | Chin | |
| 7,306,603 B2 | 12/2007 | Boehm, Jr. et al. | |
| 7,326,210 B2 | 2/2008 | Jahng et al. | |
| 7,468,064 B2 * | 12/2008 | Bruneau et al. | 606/99 |
| 7,491,208 B2 * | 2/2009 | Pond et al. | 606/104 |
| 7,491,218 B2 | 2/2009 | Landry et al. | |
| 7,497,869 B2 | 3/2009 | Justis | |
| 7,520,879 B2 | 4/2009 | Justis et al. | |
| 7,527,638 B2 | 5/2009 | Anderson et al. | |
| 7,547,318 B2 | 6/2009 | Birkmeyer et al. | |
| 7,575,581 B2 | 8/2009 | Lovell | |
| 7,588,575 B2 | 9/2009 | Colleran et al. | |
| 7,588,588 B2 | 9/2009 | Spitler et al. | |
| 7,666,189 B2 | 2/2010 | Gerber et al. | |
| 7,691,132 B2 | 4/2010 | Landry et al. | |
| 7,708,763 B2 | 5/2010 | Selover et al. | |
| 7,717,944 B2 | 5/2010 | Foley et al. | |
| 7,749,233 B2 | 7/2010 | Farr et al. | |
| 7,758,584 B2 | 7/2010 | Bankoski et al. | |
| 7,758,617 B2 | 7/2010 | Iott et al. | |
| 7,763,055 B2 | 7/2010 | Foley | |
| 7,776,051 B2 | 8/2010 | Colleran et al. | |
| 7,824,410 B2 | 11/2010 | Simonson et al. | |
| 7,846,093 B2 | 12/2010 | Gorek et al. | |
| 7,875,031 B2 * | 1/2011 | Chin et al. | 606/86 A |
| 2003/0171750 A1 | 9/2003 | Chin | |
| 2004/0039384 A1 | 2/2004 | Boehm, Jr. et al. | |
| 2005/0043742 A1 | 2/2005 | Bruneau et al. | |
| 2005/0065517 A1 | 3/2005 | Chin | |
| 2005/0131408 A1 | 6/2005 | Sicvol et al. | |
| 2005/0131421 A1 | 6/2005 | Anderson et al. | |
| 2005/0131422 A1 | 6/2005 | Anderson et al. | |
| 2005/0192570 A1 | 9/2005 | Jackson | |
| 2005/0192589 A1 | 9/2005 | Raymond et al. | |
| 2005/0228380 A1 | 10/2005 | Moore et al. | |
| 2006/0030872 A1 | 2/2006 | Culbert et al. | |
| 2006/0089652 A1 | 4/2006 | Eckman | |
| 2006/0234279 A1 | 10/2006 | Hawkes et al. | |
| 2006/0235279 A1 | 10/2006 | Hawkes et al. | |
| 2006/0241600 A1 | 10/2006 | Ensign et al. | |
| 2006/0264942 A1 | 11/2006 | Lim et al. | |
| 2006/0264962 A1 | 11/2006 | Chin et al. | |
| 2007/0016188 A1 | 1/2007 | Boehm, Jr. et al. | |
| 2007/0016198 A1 | 1/2007 | Boehm, Jr. et al. | |
| 2007/0016199 A1 | 1/2007 | Boehm, Jr. et al. | |
| 2007/0073294 A1 | 3/2007 | Chin et al. | |
| 2007/0078460 A1 | 4/2007 | Frigg et al. | |
| 2007/0093814 A1 | 4/2007 | Callahan, II et al. | |
| 2007/0106123 A1 | 5/2007 | Gorek et al. | |
| 2007/0167954 A1 | 7/2007 | Sievol et al. | |
| 2007/0191840 A1 | 8/2007 | Pond, Jr. et al. | |
| 2007/0219854 A1 | 9/2007 | Mueller et al. | |
| 2007/0233079 A1 | 10/2007 | Fallin et al. | |
| 2007/0233097 A1 | 10/2007 | Anderson et al. | |
| 2007/0239159 A1 | 10/2007 | Altarac et al. | |
| 2007/0239259 A1 | 10/2007 | Altarac et al. | |
| 2007/0270842 A1 | 11/2007 | Bankoski et al. | |
| 2007/0299443 A1 | 12/2007 | DiPoto et al. | |
| 2007/0299444 A1 | 12/2007 | DiPoto et al. | |
| 2008/0009864 A1 | 1/2008 | Forton et al. | |
| 2008/0015582 A1 | 1/2008 | DiPoto et al. | |
| 2008/0039838 A1 | 2/2008 | Landry et al. | |
| 2008/0045957 A1 | 2/2008 | Landry et al. | |
| 2008/0071274 A1 | 3/2008 | Ensign | |
| 2008/0077139 A1 | 3/2008 | Landry et al. | |
| 2008/0086130 A1 | 4/2008 | Lake et al. | |
| 2008/0097457 A1 | 4/2008 | Warnick | |
| 2008/0114403 A1 | 5/2008 | Kuester et al. | |
| 2008/0119849 A1 | 5/2008 | Beardsley et al. | |
| 2008/0119850 A1 | 5/2008 | Sicvol et al. | |
| 2008/0125788 A1 | 5/2008 | Cohen et al. | |
| 2008/0125817 A1 | 5/2008 | Arnett et al. | |
| 2008/0140075 A1 | 6/2008 | Ensign et al. | |
| 2008/0140120 A1 | 6/2008 | Hestad et al. | |
| 2008/0140132 A1 | 6/2008 | Perez-Cruet | |
| 2008/0262318 A1 | 10/2008 | Gorek et al. | |
| 2009/0082819 A1 | 3/2009 | Blain et al. | |
| 2009/0221878 A1 | 9/2009 | Gorek | |
| 2009/0221879 A1 | 9/2009 | Gorek | |
| 2009/0222044 A1 | 9/2009 | Gorek | |
| 2009/0222045 A1 | 9/2009 | Gorek | |
| 2009/0222046 A1 | 9/2009 | Gorek | |
| 2009/0234392 A1 | 9/2009 | Dziedzic et al. | |
| 2009/0287061 A1 | 11/2009 | Feigenbaum et al. | |
| 2010/0049206 A1 | 2/2010 | Biyani | |
| 2011/0196429 A1 | 8/2011 | Hua | |
| 2011/0270324 A1 | 11/2011 | Hua | |
| 2011/0282390 A1 | 11/2011 | Hua | |
| 2011/0301647 A1 | 12/2011 | Hua | |
| 2012/0016422 A1 | 1/2012 | Hua | |

FOREIGN PATENT DOCUMENTS

| | | |
|---|---|---|
| WO | WO 2008/136802 A1 | 11/2008 |
| WO | WO 2010/039817 A2 | 4/2010 |
| WO | WO 2010/039817 A3 | 7/2010 |
| WO | WO 2010/039817 A4 | 9/2010 |
| WO | WO 2011/040986 A1 | 4/2011 |

OTHER PUBLICATIONS

U.S. Appl. No. 13/122,388, filed Apr. 1, 2011, Hua.
U.S. Appl. No. 13/082,346, filed Apr. 7, 2011, Hua.
U.S. Appl. No. 13/189,432, filed Jul. 22, 2011, Hua.
U.S. Appl. No. 13/245,227, filed Sep. 26, 2011, Hua.
Notification of Transmittal of the International Search Report and the Written Opinion of the International Searching Authority, or the Declaration dated May 25, 2010 for International Application No. PCT/US2009/059004.
Notification of Transmittal of the International Search Report and the Written Opinion of the International Searching Authority, or the Declaration dated Oct. 18, 2010 for International Application No. PCT/US2010/029199.
International Preliminary Report on Patentability for International Application No. PCT/US2009/059004 dated Apr. 14, 2011.
Notification of Transmittal of the International Search Report and the Written Opinion of the International Searching Authority, or the Declaration dated Jul. 6, 2011 for International Application No. PCT/US2011/030612.
Medtronic Sofamor Danek METRx System Surgical Technique "Minimal Access Spinal Technologies" article, 22 pages, 2004.
2010 K2M Complex Spine Innovations, Mesa Spinal System Lumbar Products for Surgeons Treating Spinal Disorders, 1 page.
2009 K2M Complex Spine Innovations, Serengeti Minimally Invasive Retractor System, A Simple Approach to Complex Spine, 2 pages.

* cited by examiner

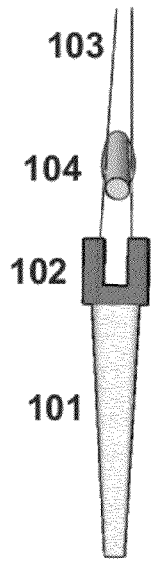 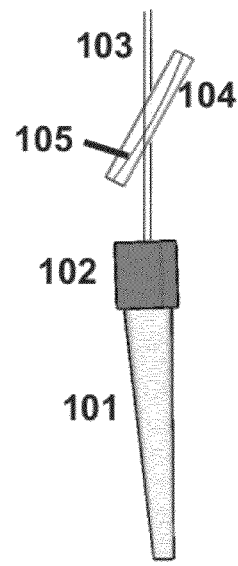 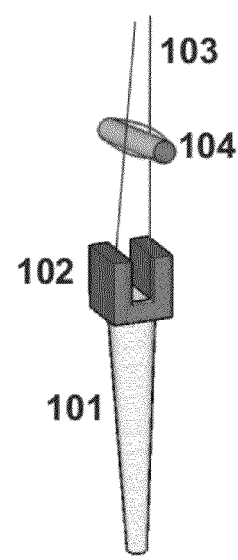
FIG. 9A  FIG. 9B  FIG. 9C
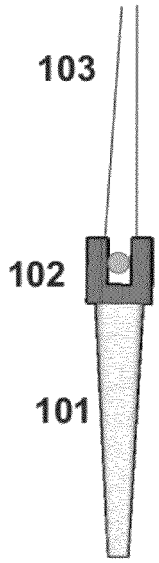 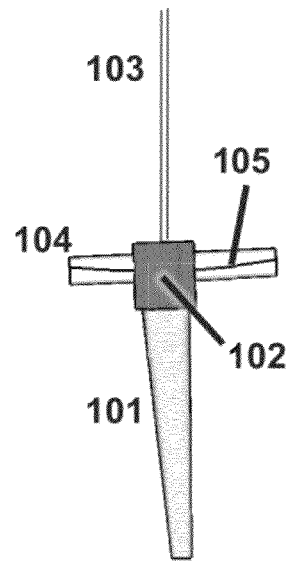 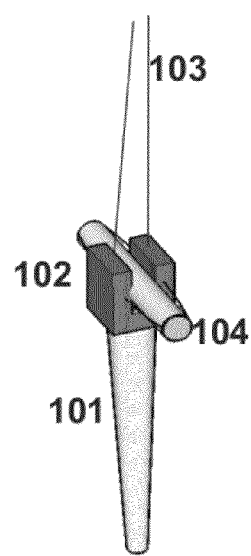
FIG. 9D  FIG. 9E  FIG. 9F

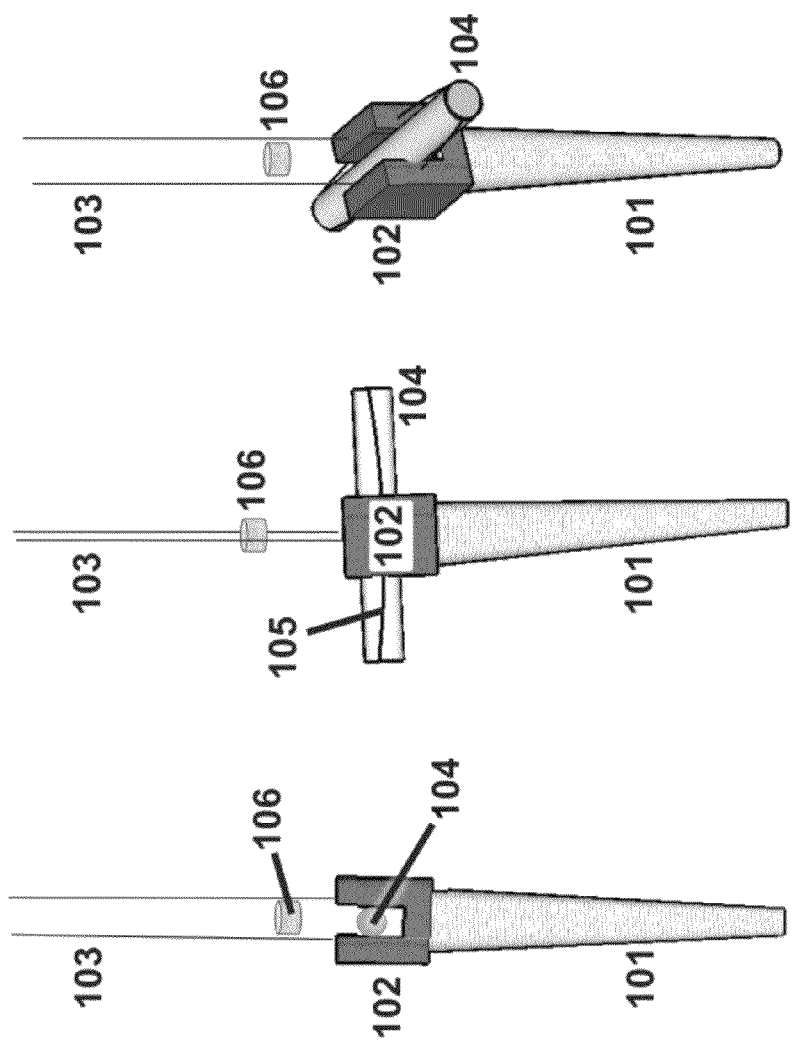

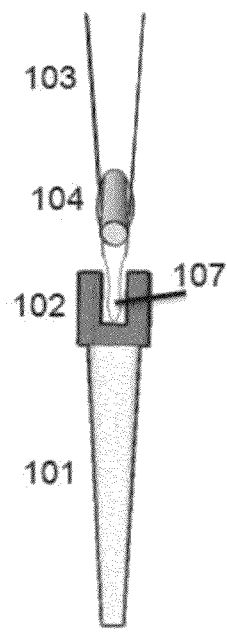 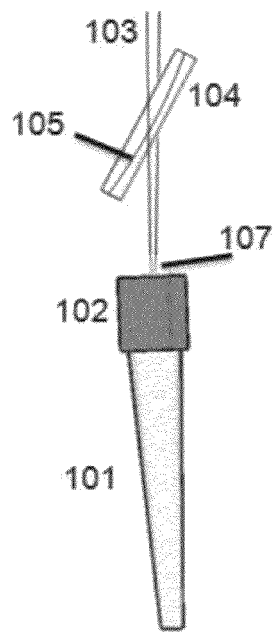 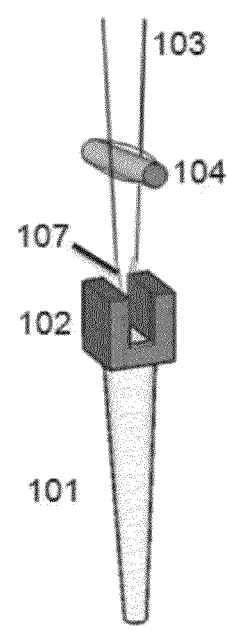
FIG. 11A    FIG. 11B    FIG. 11C
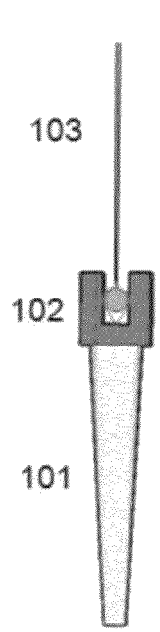 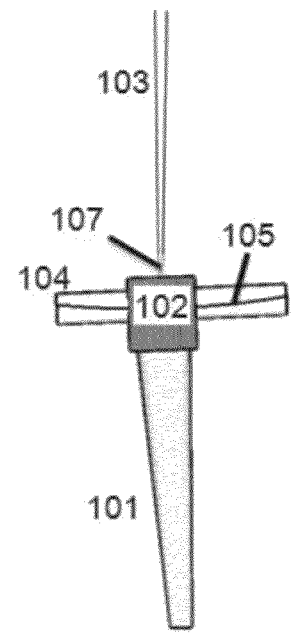 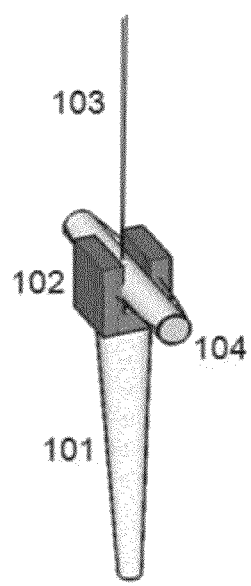
FIG. 11D    FIG. 11E    FIG. 11F

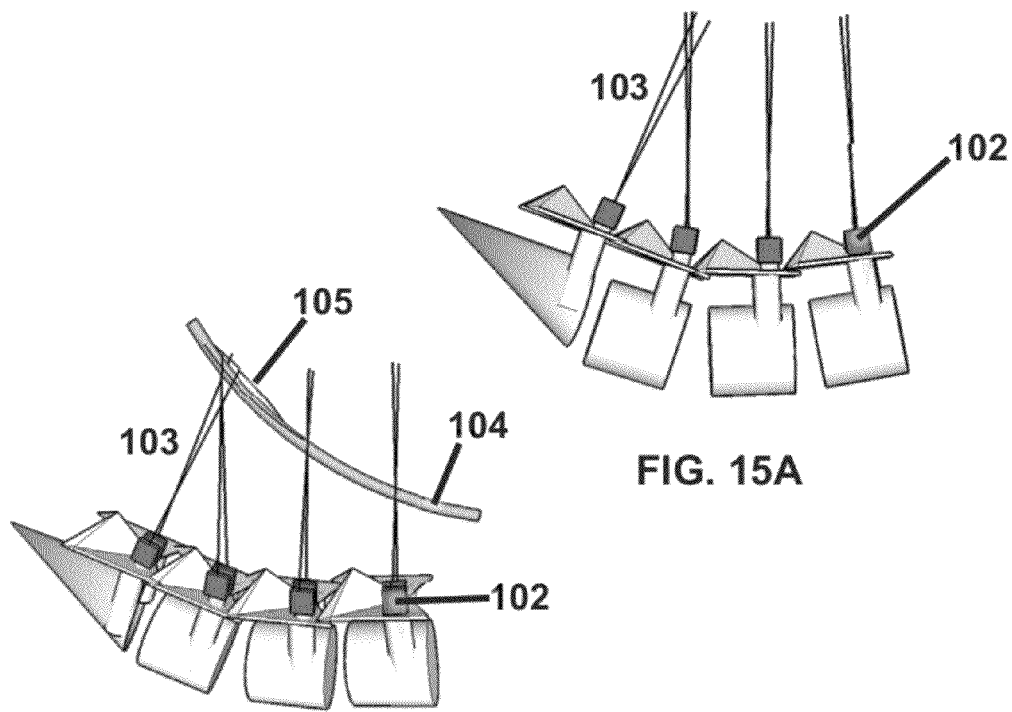
FIG. 15A
FIG. 15B
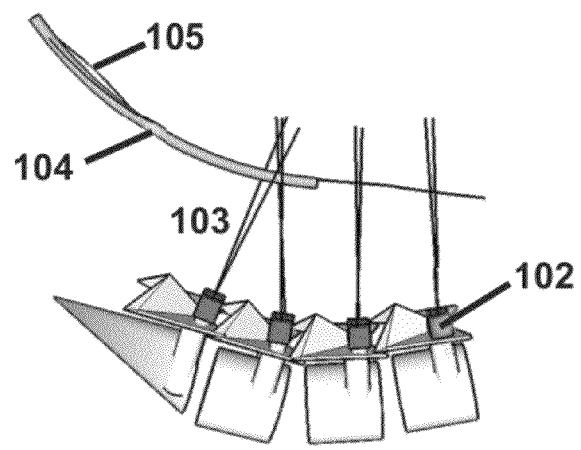
FIG. 15C

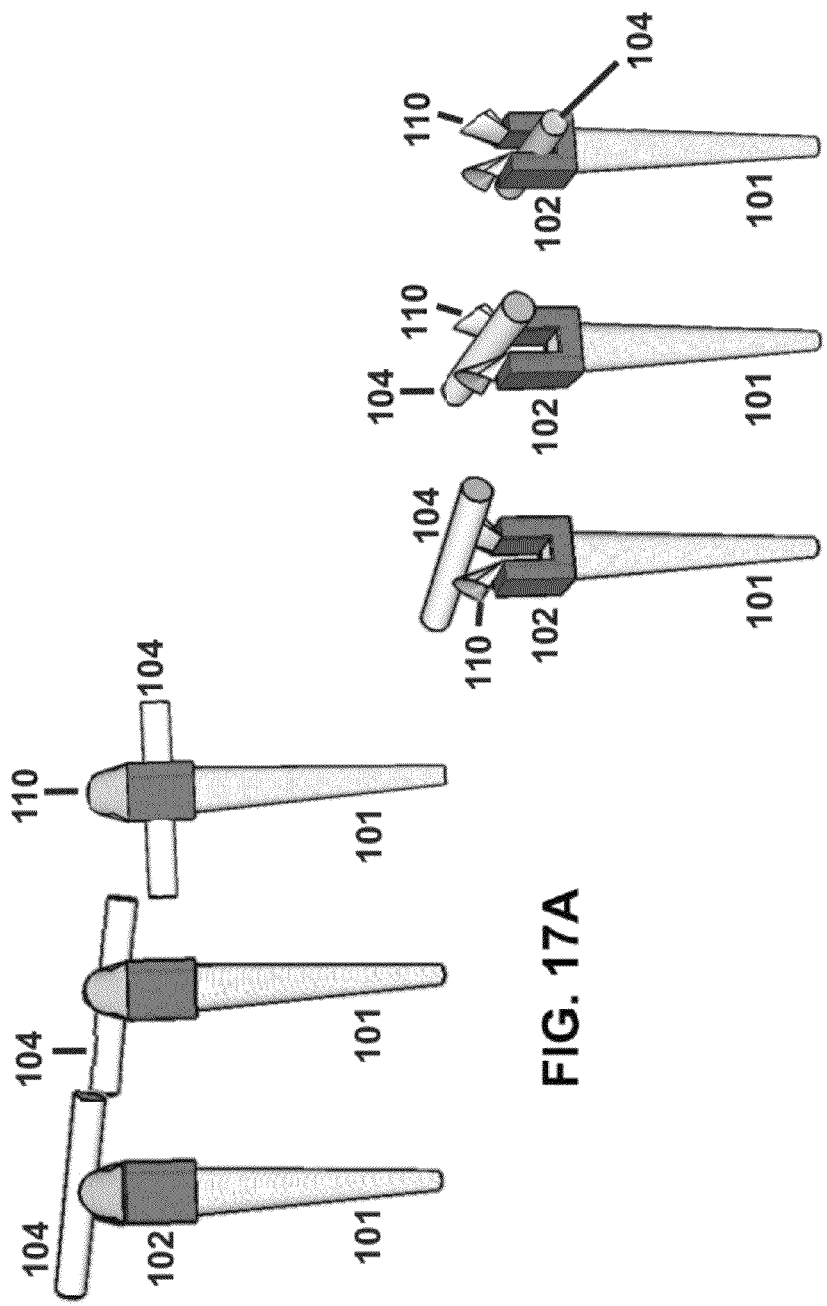

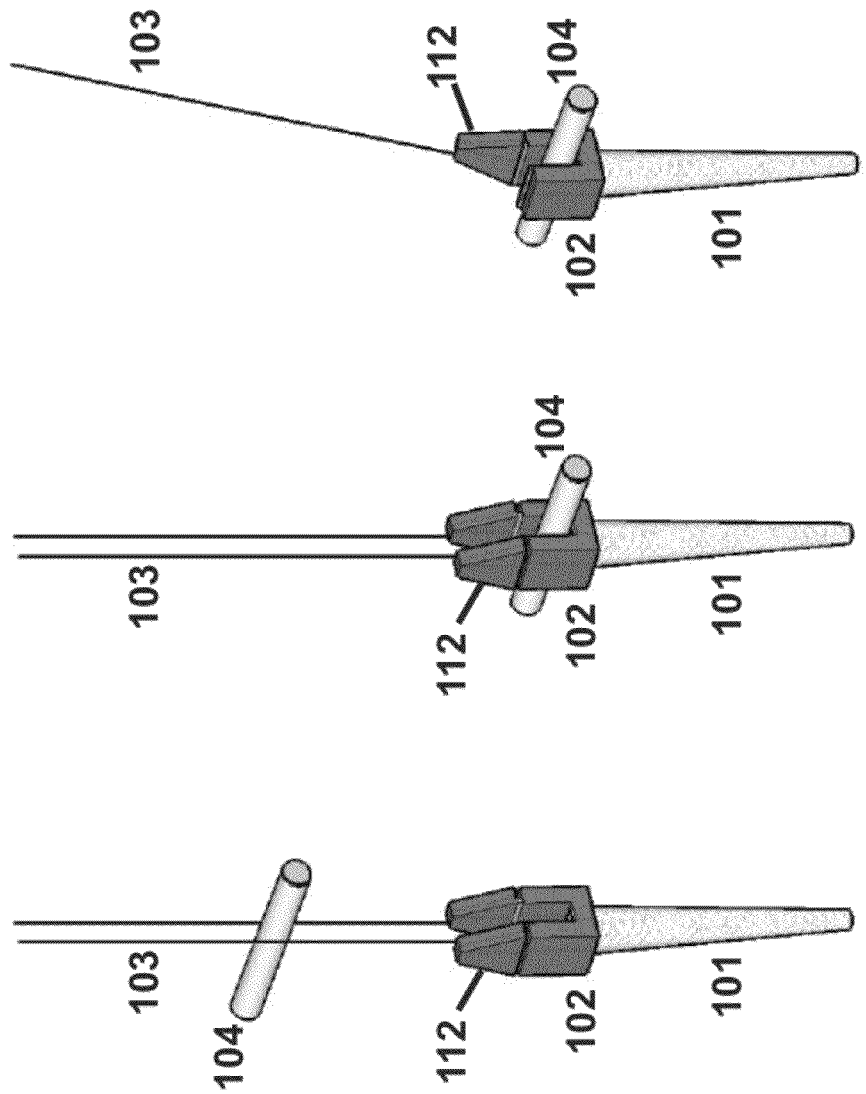

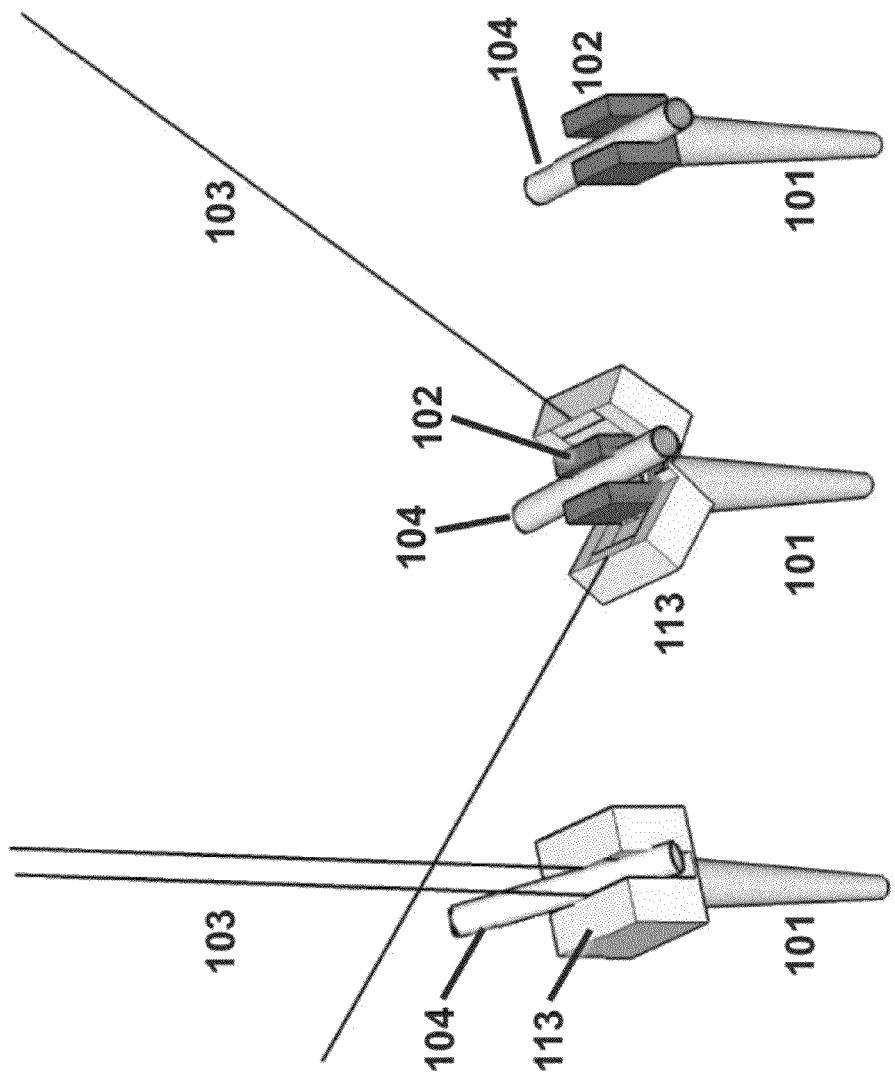

SYSTEM AND METHOD FOR WIRE-GUIDED PEDICLE SCREW STABILIZATION OF SPINAL VERTEBRAE

CROSS-REFERENCE TO RELATED APPLICATIONS

This application is a continuation of U.S. patent application Ser. No. 13/122,388, filed Apr. 1, 2011, which is a U.S. National Phase application under 35 U.S.C. §371 of International Patent Application No. PCT/US2009/059004, filed Sep. 30, 2009, and published in English on Apr. 8, 2010, which claims priority to U.S. Provisional Application 61/101,932, filed Oct. 1, 2008. The entirety of each of the foregoing applications is hereby incorporate by reference.

BACKGROUND OF THE INVENTION

1. Field of the Invention

The present invention relates to medical devices, systems and methods for bone fixation. Specifically, the invention is directed to stabilize adjoining vertebrae in the cervical, thoracic, and lumbosacral spine. More specifically, the invention is directed to fusion or stabilization of vertebrae in the lumbar spine to alleviate axial back pain. Most specifically, the invention is directed to improving minimally invasive surgical (MIS) approaches to pedicle screw fusion by reducing the number and size of incisions and the size of the medical instruments inserted therein.

2. Description of the Related Art

While some lower back conditions can be ameliorated with non-surgical approaches, spinal fusion is recommended for certain conditions when non-surgical approaches fail. Non-surgical approaches include medications, physical therapy, chiropractic treatment, traction, epidural steroid injections, facet blocks or rhizotomy, weight loss, smoking cession, and acupuncture. Conditions that commonly serve as indications for spinal fusion or stabilization surgery can be divided generally into three categories: (i) trauma induced, (ii) curvature, and (iii) degenerative.

Trauma induced conditions include fractures and ligamentous injuries. Fractures typically result from an unfortunate incident involving an extraneous force or fall but may also arise from pathologic conditions, such as cancer or osteoporosis. Fractures are often compressive in nature and typically lead to a pathological curving of the spine resulting in a loss of the natural lordotic curvature in the lumbar and cervical spine, known as kyphosis. Fractures of the spine also occur with translational or rotational forces perpendicular to the axis of the spine. These forces result in fractures of the facet or pars interarticularis (pars). If the external forces are large enough, vertebrae can collapse resulting in a burst fracture that can injure all 3 columns of the vertebrae (anterior, middle, and posterior columns). Many traumatic injuries can heal without surgery, but unstable injuries that pose a risk for neurologic injury and/or pain require stabilization through a procedure such as fusion.

A condition called spondylolisthesis characterized by slippage of the spine bones or vertebrae relative to one another can result from fractures of the pars interarticularis (pars fracture) known as spondylolysis. Spondylolisthesis can also develop from malformation of the facet joints by degenerative arthritis as well as congenital malformation and pathologic conditions such as tumors. If the pars on both sides are fractured, then the spinous process and lamina are essentially completely disconnected from the pedicle and vertebral body. This large fragment is called the Gill body. Pars fractures are actually common in people of all ages (often acquired in the teenage years). While, many of these patients are mildly symptomatic and do not require surgery, those with progressive symptoms may require surgical decompression with or without fusion. Spondylolisthesis results in misalignment of the spine and increases the risk of a nerve becoming entrapped. Nerves travel within the spinal canal bounded by the vertebrae and their roots protrude from the curved openings in the sides of the vertebrae called foramina (singular is foramen). These spinal nerves are suspected to be the source of back and radicular pain when they become entrapped or when the nerve endings become irritated by irregular or abrasive motion around a disc, bone, or joint. Spondylolisthesis can also aggravate or be accompanied by degeneration of disc or facet joint which can lead to axial back pain.

The normal curvature of the lumbar and cervical spine is lordosis, where the posterior aspect of these spinal levels forms a concave curve. The thoracic spine normally has a kyphotic or convex curve. Curvature conditions include straightening of the natural curvature as well as abnormal lordosis, abnormal kyphosis or lateral/rotational bending called scoliosis. Curvature conditions can occur idiopathically during adolescence, i.e. adolescent idiopathic scoliosis, or develop as a secondary problem in situations where spinal muscle activation is abnormal such as cerebral palsy, spina bifida, or tethered cord syndrome. Abnormal spinal curvature is common in spinal degeneration when the discs and joints degenerate asymmetrically leading to a progressive curvature (scoliosis, kyphosis, or lordosis) as the biomechanics of the spine are disrupted. Curvature conditions also occur after trauma with compression or burst fractures or with ligamentous injury. Additionally, curvature conditions can occur iatrogenically after previous spinal surgery where the anatomy and biomechanics of the spine have been altered. Such situations include the removal of the posterior tension band after laminectomy as well as the alteration of physiologic movement after spinal fusion leading to adjacent level compensation and degeneration. Curvature conditions lead to abnormal biomechanical stress on the discs and facet joints accompanied by compensatory measures such as facet or ligamentous hypertrophy. Patients can develop both axial back pain and radicular pain. In patients who have failed conservative therapy and bracing, surgery can be effective. Surgery in these conditions includes decompression of nerve or spinal cord compression as well as fusion or stabilization. Curvature can be corrected through surgery, and fusion prevents further curvature from developing.

Degenerative conditions include spinal arthritis and recurrent disc herniation. Spinal arthritis is the most common indication for fusion and may exist in the form of severe disc degeneration (also called Degenerative Disc Disease, DDD) or facet disease. Degenerative arthritis can also be a cause of spondylolisthesis in addition to traumatic fractures discussed above. Degenerative conditions are generally accompanied by nerve compression causing radicular pain in the distribution of the nerve's receptive field, which usually correlates with and is manifested in arm or leg pain. Pure nerve compression syndromes such as herniated nucleus propulsus (herniated discs) or foraminal stenosis (narrowing of the side foramina canals through which the nerves pass) can often be treated with decompression without fusion. Pure disc degeneration syndromes can be treated with fusion without decompression of the nerves. However, most commonly disc degeneration occurs in combination with nerve compression causing both axial back pain and radicular limb pain. In these circumstances fusion surgery is combined with nerve decompression surgery.

Fusion functions to eliminate motion in the disc space and facet joints between adjacent vertebrae. The vertebrae provide the rigid structural framework of the spine and the fibrocartilagenous disc space acts as a cushion or shock-absorber. Degradation of the disc space can distort alignment and alter the biomechanical cushion that the disc affords the adjacent vertebrae. This degradation alters the forces impacted upon the vertebrae and results in axial back pain. Fusion is designed to eliminate movement between adjacent vertebrae by either forming a solid bridge of bone across the disk space and/or creating new bone formation in the posterolateral space to provide stabilization, rigidity, and strength. Sometimes fusion involves a bone graft taken from another location in the body (i.e. autograft from the iliac crest in the pelvis) or from an external source, i.e. allograft. Physicians commonly refer to the level of a fusion. A single level fusion involves stabilizing the two vertebral bones adjacent to a diseased disc. A two-level fusion involves stabilizing three adjacent vertebral bones spanning two problematic disc spaces. Each vertebra makes contacts (joints) with adjacent vertebrae at three points, the paired facet joints located posteriorly and the intervertebral disc located anteriorly. Thus, lumbar fusion can be directed either at the posterior facet joints or at the anterior interbody/disc space or both. When an anterior interbody fusion is performed in combination with posterior fusion, the procedure is termed 360° fusion. One commonly used technique of posterolateral fusion is pedicle screw fusion where screws are directed into the pedicle portions and the bodies of adjacent vertebrae and then rods are connected to the screws across the disc spaces. The screws and rods hold the adjacent vertebrae motionless relative to one another and allow the bone graft that is placed either in the interbody (disc) space or in the posterolateral space to grow into solid bone. Conventional pedicle screws and rods are metal, typically titanium (Ti) alloy but have been made from stainless steel as well. Recently rods have been made from a minimally flexible polymer called polyetheretherketone (PEEK).

Interbody fusion involves placing one or more spacers (typically pre-loaded with bone graft material) within the interbody (disc) space between bony vertebral bodies after the degenerated disc has been cleaned out and removed. Spacers are made from bone grafts, titanium, carbon fiber, or polymers such as PEEK. Interbody fusion can be performed through several approaches including: an anterior approach (anterior lumbar interbody fusion, ALIF), a posterior approach (posterior lumber interbody fusion, PLIF, or transforaminal lumbar interbody fusion, TLIF), or a lateral approach (direct lateral interbody fusion, DLIF™—Medtronic, or extreme lateral interbody fusion, XLIF™—Nuvasive). The aim of these approaches is to remove the degenerated disc and replace the disc with material that induces bony fusion. Alternatively the disc can be replaced with an artificial joint/disc (discussed below). Each of these interbody approaches has advantages and disadvantages. Anterior procedures require a retroperitoneal dissection and risk injury to the large blood vessels anterior to the lumbar vertebrae. Also injury to the nerve plexus anterior to the vertebrae can result in sexual dysfunction. The lateral approach is promising but is limited to the upper and mid lumbar levels (rostral to L5,S1) because of obstruction by the iliac crest. The posterior interbody approach is more time consuming and typically requires more muscle dissection and retraction. However, the posterior approach allows the placement of the interbody graft, posterior pedicle screw fusion, and decompression of nerves all to occur through the posterior incision(s).

Although anterior and lateral approaches can be performed stand-alone (without posterior instrumentation), many surgeons will back-up or supplement anterior or lateral interbody fusions by placing pedicle screws posteriorly after the interbody cage or graft has been placed. This 360° fusion limits movement more than just an isolated anterior or posterior fusion, and fusion rates are increased. However in ALIF and lateral interbody (DLIF, XLIF) cases, two sets of incisions are required for a 360° fusion.

The posterior approaches (TLIF and PLIF) allow an interbody fusion, pedicle screw fusion, and neural decompression to be done all through the same posterior incision(s). In the TLIF, a single large interbody spacer is inserted on the side ipsilateral to the patient's symptomatic side after neural decompression is completed. If both sides are symptomatic then decompression is required on both sides. A PLIF is performed by placing two interbody spacers, one on each side. Posterior procedures may be done according to: (i) an invasive open procedure in which a large incision and/or several incisions are made, (ii) a percutaneous approach in which small incisions and/or few incisions are made, and potentially (iii) an endoscopic approach in which small incisions are made and all tools and devices are inserted through portals with visualization provided on an external monitor.

As an alternative to fusion, recent advances in interbody stabilization have resulted in the development of artificial disc technology. Artificial discs replace the degenerated discs and allow continued motion at the joint. Both cervical and lumbar artificial discs have been developed. Additionally, dynamic stabilization techniques have been developed for the posterior spine. These posterior techniques utilize pedicle screws and a dynamic rod. Typically the dynamic rod has a mechanism to bend under certain loads or forces, thereby absorbing some stress and strain that is applied to the spine. The advantage of dynamic stabilization is that motion is preserved in the spine. However, the durability of these systems may be an issue. In fusions, the bone graft (interbody or posterolateral) eventually fuses the vertebrae eliminating the need for the spinal instrumentation (screws and rods). However in dynamic stabilization, fusion does not occur so the screws and dynamic rods will always be subjected to the strain and forces of the spine. Over time the possibility of loosening of the pedicle screws or mechanical failure may increase. Sometimes the use of a slightly flexible rod such as a rod made of PEEK may actually increase fusion by reducing stress shielding. Stress shielding occurs with rigid fusion constructs that shields the vertebral bone in contact with the bone graft from the stresses required to form and remodel bone.

Posterior lumber stabilization (fusion and dynamic stabilization) techniques have evolved into minimally invasive approaches because such minimized exposures reduce patient morbidity and facilitate patients' recovery to function. Blood loss and hospital stays are shorter. The process of performing a minimally invasive pedicle screw fusion is the same as that for dynamic stabilization and involves two basic parts. First, screws are placed percutaneously through the pedicle into the vertebral body. For minimally invasive systems, cannulated screws are placed percutaneously over a fluoroscopically (an X-ray that can be seen on a video screen) guided wire. Generally, two screws are used on each vertebral body being fused, one on a right side and the other on a left side. The second part of the process involves connecting the screws with a rod and locking the rod and screws together. In dynamic stabilization, the rod or rod-like device (flexible connector) is bendable, but the process of inserting this bendable rod is the same as that for fusion. For example, a rod-like device (flexible connector), like a rod, fits within the screw heads, but may also include an element (a shock absorber, a spring, etc.) that allows some motion. The variations between different minimally invasive systems mostly arise in the method of placing the rod and locking the rod with the screws through a minimal incision.

After the screws are inserted and before the intervertebral body spacer is inserted, the damaged or degenerated disc within the disc space must be removed. In the TLIF approach, the disc space is accessed through a facetectomy in which the foramen around the nerve roots is opened with a bone-cutting tool such as an osteotome or a high speed drill. In the PLIF approach, laminectomies or laminotomies are performed to access the disc space. Both TLIF and PLIF allow for decompression of the spinal thecal sac and the nerve roots; however, the facetectomy in a TLIF allows the maximum decompression of the exiting nerve root on that side. With gentle retraction of the thecal sac, the disc space is easily accessed. Then the instruments used for clearing out the degenerated disc may be inserted into the disc space to complete the discectomy.

Following removal of the disc, the surgeon should prepare the bony surfaces, known as the end plates, of the vertebral bodies on each side of the disc that was removed. Peeling off the end plate with a tool such as a curette induces bleeding which stimulates healing and assimilation of the bone graft to be inserted into the interbody space. The spacer or cage that is to be inserted is typically constructed of bone, titanium, carbon fiber, or polymers such as PEEK. The spacer is usually hollow or at least porous to accommodate bone graft material therein. Bone inducing protein such as bone morphogenetic protein (BMP) is also commonly placed within the spacer. After placing the spacer and bone graft, the rods may be inserted into the pedicle screws and the screws can be tightened to lock the rods in place.

Typically the placement of the percutaneous screws is fairly straight forward. The insertion of the rod through the screw heads and locking of the rod with the screws are the steps that are currently most difficult through a minimal incision. In most of the minimally invasive surgery (MIS) systems used today, a guide wire is placed percutaneously under fluoroscopic guidance through the pedicle. Then, dilating tubes and finally a tower is inserted over the wire to both dilate the tissue and also allow the screw to be placed through the tower. Therefore, the tower has to be larger than the maximum diameter of the screw head. Once the towers are in place and screws have been placed in each tower, the rod is then inserted through one of a variety of methods. The leading MIS system is Sextant™ by Medtronic. In this system, the rod is placed by forming a pendulum like mechanism. The two or three towers (for one or two-level fusion, respectively) are coupled together to align the towers, and the rod is swung around through a separate incision superior or inferior to the towers in a pendulum fashion. Once the rod is swung in place, locking caps are placed through the towers and tightened. Alternatively, most of the other systems insert the rod through one of the towers and then turn the rod approximately 90° to capture the other screws in the other towers. Inserting the rod through the screw heads in a minimally invasive system is done blindly, i.e. without direct visualization of the screw head. Thus this process is sometimes tedious and frustrating.

The Sextant™ system and other systems that use towers are limited by both the number of incisions required and the size of each incision. The use of a separate tower for each screw requires a separate incision for each screw. The Sextant™ system also requires an additional incision for the rod, equaling six incisions (three on each side) for a single level fusion and eight incisions for a two level fusion. The other tower systems that use the direct rod insert and turn mechanism still require one incision for each screw and each incision has to be larger than the size of a tower through which the screws are inserted. Typically, each incision is at least 15 mm in length.

U.S. Pat. No. 7,306,603 entitled "Device and method for percutaneous placement of lumbar pedicle screws and connecting rods" by Frank H. Boehm, Jr., et al. and assigned to Innovative Spinal Technologies (Mansfield, Mass.) discloses a system of connecting a rod to the pedicle screws using a pin and recesses within the screw heads. According to this system the rod can pivot about a longitudinal axis of the pin between a first position in which the rod is parallel to the longitudinal axis of the screw (i.e. vertically oriented) and a second position in which the rod is transverse to that axis in order to bridge screws on adjacent vertebrae. U.S. Pat. No. '603 teaches various guide systems (see FIGS. 5 and 6), rod holder systems (see FIGS. 8, 9, 10, and 11), and a rod guide system (see FIG. 12) but does not include a sleek, detachable wire-guided system among them. Rather, the systems illustrated are tower-like with rather bulky dilators (80 and 86 in FIGS. 6 and 8), sheaths (81 in FIG. 6), and/or outer housing (120 in FIGS. 11 and 12).

U.S. Patent Application Publication No. (hereinafter US Pub. No.) 20080140075 entitled "Press-On Pedicle Screw Assembly" by Michael D. Ensign and assigned to Alpinespine, LLC (American Fork, Utah) discloses attaching the rod to screw heads indirectly via a tulip assembly. The tulip assembly has a housing with an inner diameter smaller than an inner diameter of the screw head such that it is easily pressed into position upon the screw head. The rod is then placed by attaching directly to the tulip assembly after connecting the assembly to the screw head. The publication mentions using a Kirschner wire (or K-wire) for inserting both the pedicle screws and the tulip member (see [0030], [0032], and [0045]) but does not disclose how the rods are guided into position.

US Pub. No. 20080097457 entitled "Pedicle screw systems and methods of assembling/installing the same" by David R. Warnick and unassigned, like US Pub. No. '075, also discloses using a tulip assembly as an intervening means to join a rod to the screws. In this system, rather than a press-on locking mechanism, the structure is tightened by rotating an inner member and outer housing of the tulip assembly relative to one another. Also like US Pub. No. '075, US Pub. No. '457 mentions wires only with respect to using a K-wire to direct insertion of the pedicle screws and does not teach using wires to guide the rods.

U.S. Pat. No. 7,179,261 entitled "Percutaneous access devices and bone anchor assemblies" by Christopher W. Sievol, et al. and assigned to Depuy Spine, Inc. describes one of the several tower systems for placement of pedicle screws percutaneously. The patent describes a situation where the angle of the screws intersect and the towers may interfere with each other. This situation is rather typical in the lordotic lumbar spine, especially the lumbo-sacral junction. In order to solve this problem, they describe cut-outs in the tubes so that two tubes can intersect. Given that the angles of the vertebrae are variable from patient to patient and the depth of the vertebrae from the skin is also highly variable, the variations on the cutouts would have to be numerous. The present invention would provide the maximum form of "cut-out" where only wires are left. Thus interference of a number of wires from adjacent vertebrae is not a problem. Also, in the cut-out tubes taught by U.S. Pat. No. '261 the screws or any other element inserted using the tubes would still have to be inserted through the tube at some point. The cut-out tubes require that the screw (or other inserted element) is oriented longitudinally parallel to the long axis of the tube as it is directed into the body until it reaches the cut-out section, at which point it may optionally be turned perpendicularly to the long axis and directed out of the lateral cut-out. In the present invention by using the wires, the element that is inserted along them (i.e. a screw, a rod, etc.) does not have to be inserted through any lumen outside of the body. In the present invention when a screw is inserted using the wires, the wires can simply be attached to the screw head. When a rod is inserted using the same wires, the wires can simply be fed through the outer edges of the rod body, through a retaining element or clasp attached to the rod body, or between the outer edges of the rod body and a retaining element (retention thread). Thus, in the present invention it is possible for the inserted screws and rods to be oriented perpendicular to the long axis or oriented in any other manner during the entire entry pathway. This provides greater flexibility for avoiding interference between adjacent stabilization system pieces and eliminates the need for a surgeon to identify the cut-out sections before turning the screw/rod laterally and/or reorienting it. U.S. Pat. No. '261 also does not teach using the cut-out tubes for the placement of spinal fixation elements such as rods. It discloses using the cut-out tubes for screws. (See 6:9-61, 14:9-31 and FIG. 2 with slots 60, 62). If rods were inserted through the tubes and towers disclosed in U.S. Pat. No. '261, the rods would still have to be aligned parallel to the long axis of the tube (percutaneous access device) and inserted through the central lumen of the tube at the beginning, the same as for rods inserted through non-cutout tubes. The cut-out tubes are still tubes with a completely whole (not cut-out) circumference at their proximal and distal ends such that a rod could not pass entirely transversely through the tube. A rod could not pass through the tube unless parallel to the long axis within the lumen at some point such as during initial entry into the tube. In the conventional case of pedicle screw towers, the rod has to be precisely inserted through the small opening within each rigid tower. In the present invention, the wires can be manipulated (spread outward or bent) to open the encatchment area for the rod (see FIGS. 13A-13C and 14A-14C herein). For addressing spinal fixation element placement in greater detail, two related commonly owned co-pending applications are cited and incorporated by reference in U.S. Pat. No. '261. These rod placement methods are very different from that of the present invention. In published application no. 20050131422 (U.S. patent application Ser. No. 10/737,537) entitled "Methods and devices for spinal fixation element placement" everything is through a single incision (see FIG. 10-11) and a rod must be inserted through lumen of a tube/tower at some point although this point may be external to body. Inside the body, the second end of the rod must be matched up with a side slot before it can be rotated perpendicularly to the long axis of the insertion pathway. In published application no. 20050131421, U.S. patent application Ser. No. 10/738,130, especially FIG. 10-16.) In the present invention, the same wires used to guide the screws can be used to place the rods, thereby avoiding a step of inserting an additional percutaneous access device. The present invention can be used to guide rods oriented perpendicular to the long axis of the guiding element (i.e. wires) at any point along the long axis.

SUMMARY OF THE INVENTION

The present invention is directed towards improved minimally invasive (optionally adaptable for use with the percutaneous or endoscopic approach) TLIF and PLIF approaches and backing up the ALIF, DLIF, and XLIF approaches. TLIF provides several advantages including: (i) stabilization of both the anterior and posterior portions of the spine through a single posterior incision; (ii) the ability to fill with bone graft material a greater volume and diversity of spaces (front disc space with the spacer, amongst the screws and rods on the sides, and in the back of vertebrae) increasing the chances of a successful stabilization through the development and solidification of bone; (iii) the spacer placed within the front disc space maintains the natural interbody disc height to reduce pressure on nerve roots (from bone spurs, thickened, ligaments, etc.); and (iv) enhanced safety because the spinal canal is accessed from one side only and this reduces the risk of pinching, stretching, or otherwise agitating the spinal nerves.

The invention provides a Microfusion™ product for performing a minimally invasive posterior and/or transforaminal lumbar pedicle screw fusion or stabilization procedure. Hereinafter references to "fusion" implicitly include stabilization which offers somewhat greater motion short of completely fusing the bone. Likewise, hereinafter references to "stabilization" implicitly include fusion. The main situations in which a surgeon can use the Microfusion™ system are similar to the situations in which the Sextant™ system from Medtronic is used. These situations include a minimally invasive TLIF procedure with either: (i) a micro-lumbar interbody fusion, MLIF™, or (ii) mini-open TLIF on the symptomatic side to decompress the neural compression, and a pedicle screw fusion through a minimally invasive incision on the contralateral side. Similarly the Microfusion™ system herein would be used bilaterally in a PLIF approach with the decompression and interbody spacer placement performed bilaterally. Alternatively, the Microfusion™ system is ideal for "backing up" (with a minimal posterior incision) anterior interbody fusions (ALIF) and lateral interbody fusions (XLIF™ and DLIF™) MLIF™ collectively encompasses (i) transforaminal lumbar interbody fusions and stabilizations, (ii) posterior lumbar interbody fusions and stabilizations, (iii) anterior lumbar interbody fusions and stabilizations, and (iv) lateral lumbar interbody fusions and stabilizations through a minimally invasive "micro" approach using the guidance system described herein. Since the lateral fusions are truly minimally invasive, a minimal posterior incision for pedicle screw fusion would be very complementary. Lateral interbody fusions are becoming more popular and more spine companies are coming out with their own lateral interbody fusion systems.

The lumbar spine has a lordotic curvature such that the lowest levels, L4, L5 and S1, are posteriorly oriented, while the mid levels, L2-L3, are straight or anteriorly oriented. This curvature sets up a unique situation in which the trajectories through the pedicles (the trajectories to insert the pedicle screws) from L2 to S1 are not parallel. Rather, the trajectories commonly intersect at a point just posterior to the skin. This configuration is similar to the spokes of a wheel in which the spokes (trajectories) meet at a common center point (a hub). Given that many patients have such a lordotic configuration of the lumbar spine, it is possible to insert pedicle screws through a single incision centered in the middle of the lumbar curvature. However, if each screw required a separate tower (or tube) (as in conventional tower/tube systems) in order for multiple screws to exist simultaneously, then the sum cross sectional area of the towers/tubes does not permit a single small incision. The towers/tubes interfere with each other and get in the way of one another due to their size.

An alternative method is necessary to in order to minimize the number and size of incisions. Reducing the number and size of incisions minimizes the tissue trauma needed to place pedicle screws for lumbar stabilization or fusion. An ideal system and procedure would take full advantage of the natural curvature of the lumbar spine in order to provide this reduction.

One objective of the present invention is to provide a simple method to place two or more pedicle screws through one small hole. This provides a better cosmetic and functional result with just a single skin incision of small size (approximately 1 to 2 cm in length) regardless of the number of screws used.

Another objective of the present invention is to be able to insert, position, and manipulate a rod and a locking assembly through the same small incision in order to lock the rod within the screws. The invention provides novel ways to insert a rod into pedicle screws and ways to lock the rod within the screws through a single small incision. The method involves the attachment of one or more flexible yet firm wires (or threads, strings, cords, cables, etc.) to each pedicle screw head to be used to guide the rod down to the screw. By using flexible wires instead, the towers/tubes currently used with each screw are not needed. The screws, rods, and locking assemblies can all be placed through a single small incision and yet still be appropriately interconnected within because of the natural lordotic curvature of the lumbar spine. By attaching at least one wire on each side of the screw head, the two or more symmetrically balanced wires assist to align the screw head. The wires also trap or restrict displacement of the rod, forcing it to fit between the wires and directly into the screw head.

The wires can also be used to guide the locking assemblies down to the screw heads for embodiments in which the locking assembly is not part of the screw head itself (and already down there). In such embodiments, wire guidance is not needed for the locking assembly because it is built into or part of the screw head. Examples of this latter situation are a hinged door over the rod that swings and snaps into position to hold the rod in place in the screw head. In this situation the built-in locking assembly (on the screw head) is inserted into the pedicle contemporaneously with the screw.

In a preferred embodiment, the locking assembly is also guided down to the screw by small loops placed on the sides of the insertion tools. The wires pass through these loops (the loops pass over the wires) to guide the insertion tools down to the screws to deposit (i.e. drop off or detach) the rods and locking means. Due to the flexibility of the wires coupled with their ability to possess a high strength while maintaining a small diameter, several of them can coexist simultaneously even in a small incision.

An alternative embodiment is a hybrid system where each screw is placed through short towers that do not come to the skin surface. Wires are attached to the top of the towers so that the screw, rod, locking assembly, and tools used for insertion, adjustment, locking, compression, distraction, and removal are guided by the wires close to the skin but through individual towers close to the bone and pedicle screw. This hybrid system offers both the advantages of the wires in which many wires can overlap in a single incision at the skin level and the advantages of a tower system are preserved at the bone level. Some surgeons who are comfortable with the tower system but who want the advantages of the wire system may want to use this hybrid system.

A further objective of the present invention is to reduce patient discomfort and the potential for iatrogenic injury. Providing a system and method designed for use through a single incision assists this purpose. Only one quality incision need be made. With every incision that is made there is at least a small risk of inadvertent injury, including nerve damage, even by a skilled surgeon. However, incising is not the only risky stage of the procedure, nor the only stage capable of causing patient trauma yet having the potential for improvement to reduce these risks and liabilities. Another step of the procedure commonly causing post-surgical patient discomfort and diminished motor/sensory function is placement of the rods within the screws. The wires not only guide the rods to the screws but also function to hold nerves and muscles out of the screw head for easier insertion of the rods and locking assemblies. With nerves and muscles restrained from entering the trajectories along which the rods are delivered, there is a reduced risk of pinching, tearing, or severing a nerve or muscle.

Other objectives and advantages of the invention will be set forth in the description which follows. Implicit modifications of the present invention based on the explicit descriptions will be, at least in part, obvious from the description, or may be learned by practice of the invention. Such subtle, predictable modifications and adaptations are taken to be within the scope of the present invention. Additional advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 9A-9F shows a preferred embodiment in which two guide wires are attached to the top of the screw head, one on each side. Three orientations (left to right) show the process of lowering the rod into the screw head guided by the guide wires (FIG. 9A-9C) along with the final position in which the rod is completely within the screw head (FIG. 9D-9F).

FIG. 10A-10C shows a locking assembly being lowered to attach to the screw head to secure the rod within. An instrument used to lock a locking assembly onto the screw head can also be guided by the wire but is not shown in this diagram.

FIG. 11A-11F shows another preferred embodiment in which the guide wires are connected to flexible strands. The strands are then connected to the top of the screw shaft or the base of the screw head. As the rod is lowered into the screw head, guided by the guide wires, the flexible strands wrap around the rod. Each strand is just long enough (approximately half of the circumference of the rod) to wrap around the rod so that the ends of the guide wires meet together above the rod.

FIG. 13A shows the guide wires in a neutral, straight position. FIGS. 13B and 13C show the guide wires of the two superior vertebrae (L3 and L4) splayed open so that the rod can be easily tunneled in between the wires.

FIG. 15A-15C shows two preferred embodiments of inserting a rod through guide wires that do not share an incision with the rod. Here the lowest two levels (L5 and S1) do share a single incision but the upper two levels (L3 and L4) have separate incisions. Rod retention threads only span the inferior half of the rod and only capture the guide wires of the lower two vertebrae (L5 and S1). The superior end of the rod is then pushed through the guide wires of the upper two vertebrae (middle figure). Alternatively, a thread that is attached to the superior end of the rod can be used to pull the rod through the guide wires of the upper two vertebrae. This thread can be introduced in between each set of guide wires by a large suture needle that is inserted in one incision and is pulled out of the next incision in between the guide wires.

FIG. 17A-17B shows the sequence of lowering a rod into a malaligned screw head (or, alternatively, of lowering a malaligned rod into a properly aligned screw head) using the flanged attachments as in FIG. 16A-16D. The bi-convex nature of the flanged attachments permits the rod to twist and adjust as it is lowered. Otherwise, without the flanged attachments, in a malaligned situation the rod would hit the edges of the screw head and would not be able to be lowered further. The flanged attachments are shown here as detachable elements on the screw head; however, another preferred embodiment is a flanged and convex shaped rod guide built into the tops of opposing sides of the "U" shaped screw head (i.e. may be integrally part of the screw head interior itself).

FIG. 18A-18C shows another preferred embodiment in which a wire is connected to a screw with break off extended tabs. Extended tabs are used to help reduce the rod into the screw head in cases of malalignment of the screw heads. Extended tabs are removed by snapping them off after the rod is locked in place. A wire attached to the extended tab helps to guide the rod and locking assembly into the screw head. The wire is removed when the extended tab is removed. Extended tabs that are tapered or triangular in shape also act similarly to the flanged attachments in FIG. 16A-16D and 17A-17B to guide a rod into the seat of a malaligned screw head.

FIG. 19A-19C shows another preferred embodiment in which a wire is connected to a clamp or device that holds the screw head. A preferred embodiment of the clamp or device is composed of at least two parts that can be broken apart after the rod is locked in place so that the pieces of the device can be removed with the wire. The clamp or device is attached to the screw before insertion into the bone. The clamp or device is shaped so not to impede the placement of the rod into the seat of the screw head. The parts of the clamp are held together by a thin strand that is cut or snapped apart after the rod is locked in place. The clamp or device is made from metal, polymer, or plastic materials such that no residual is left after the clamp is removed.

DETAILED DESCRIPTION OF THE PREFERRED EMBODIMENT

Figure 1A:
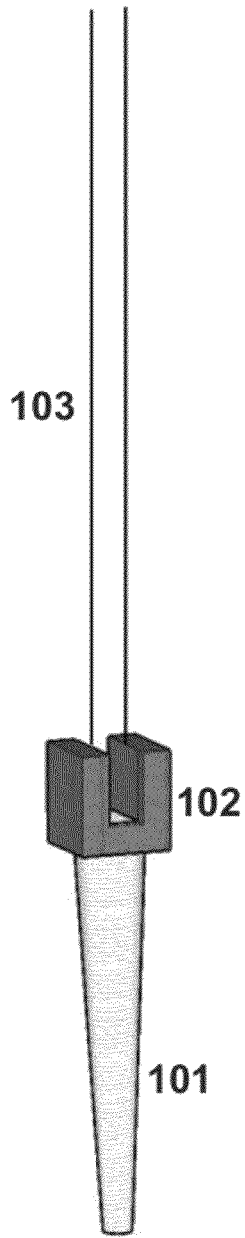
FIG. 1A-1C shows a pedicle screw with a tapered shaft directed downwards, concave U-shaped screw head, and detachable elongated guide wires directed upwards (one on each side of the head). The elongated guide wires may attach directly to the screw head (FIG. 1A) or they may attach to 2 or more short wires on each side of the screw head. This configuration creates a wire cage that forces the screw head and the rod to align with each other as the rod is lowered into the seat of the screw head.

The invention involves at least a screw, a rod, and a locking assembly being wire-guided down to pedicles of the vertebrae and the rod secured to stabilize the vertebrae. The locking assembly may be built into the screw head or be a separate element. The locking assembly may be guided down to the screw before or after insertion of the rod depending upon the details of the locking mechanism used to secure the rod. In some cases, the locking assembly is already present on the screw head before the rod is received and in other cases the rod is inserted into the screw head first and the locking assembly follows.

A preferred embodiment of the present inventive system and method is to use one wire 103 on each side of a screw head 102 such that there are two wires 103 per screw shaft 101 to securely trap a rod 104 over the screw shaft 101 within the screw head 102. This embodiment is believed to provide the most rod 104 stability for the least volume of stabilizing elements (thereby enabling a very small incision without stressing it). The wire 103 can be attached to the screw head 102 through (i) the wire itself, (ii) an extension of the wire that is formed of a material that is the same as a material from which the wire itself is derived, (iii) a thread material thinner than the wire, (iv) a short tower, or (v) an intermediate element including an extensor/extended tab 112, flexible sheet, flange 110, or mechanical device/clamp 113 as discussed further herein, among other possibilities. A single wire 103 may be attached to a screw head 102 at a single location or in two or more locations 111 as illustrated in FIG. 1A-1C.

Figure 1B:
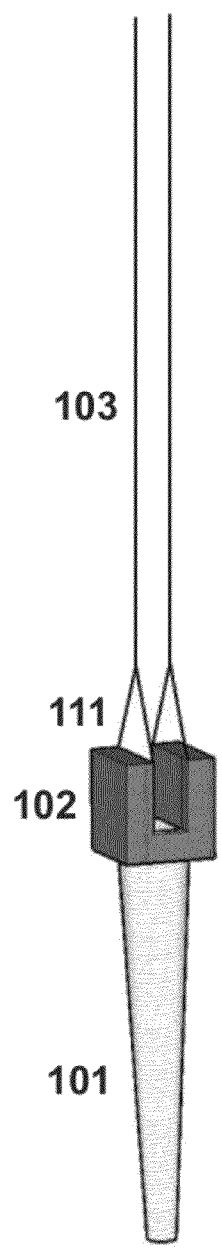
Figure 1C:
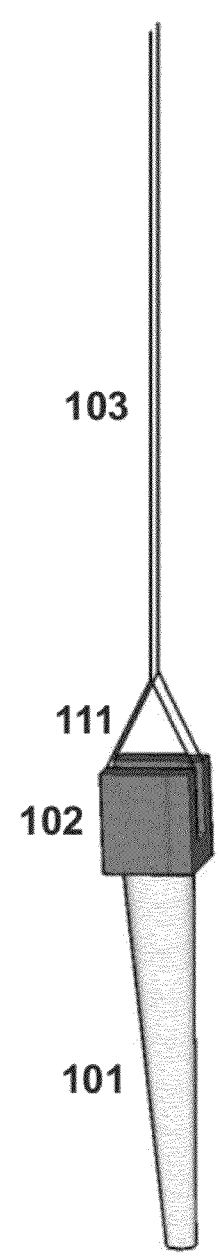

FIG. 1A-1C shows a first configuration, in which a single guide wire 103 is attached to the screw head 102 (FIG. 1A), and a second configuration, in which one more shorter wires 111 are attached to the screw head 102 and also attached to a single elongated guide wire 103 at their other end (FIG. 1B-1C). Multiple short wires 111 attached directly to the screw head 102 may provide greater stability for an easier alignment. To accommodate this multiple wire configuration 111, insertion instruments having side loops (not shown) through which the guide wire passes also have side loops to accommodate the larger area created by the fanning out configuration of the multiple short wires 111 close to the screw head 102. Thus, the side loop attached near the tip of the insertion tool will be as wide as the screw head to accommodate all the short wires at the screw head. Above the transition zone (from multiple wires 111 to a single wire 103) the insertion tool will have smaller side loops that only allow a single wire to pass.

Figure 7:
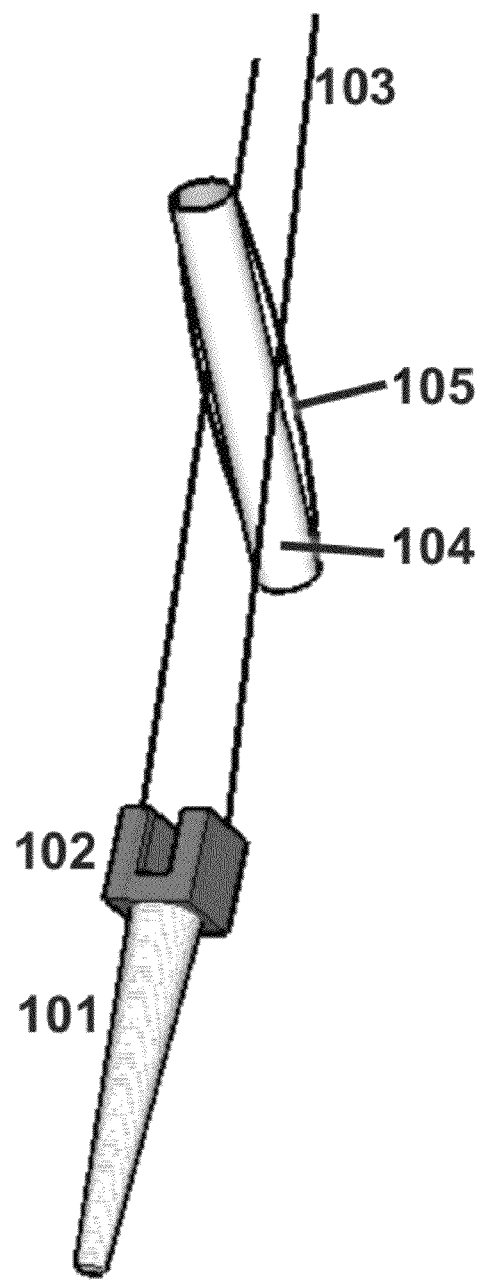
FIG. 7 shows a preferred embodiment in which the rod also has wires or threads (called rod retention threads) on each side extending between its longitudinal ends to form a loop with the body of the rod for securing the rod along the screw head wires during placement.
Figure 8:
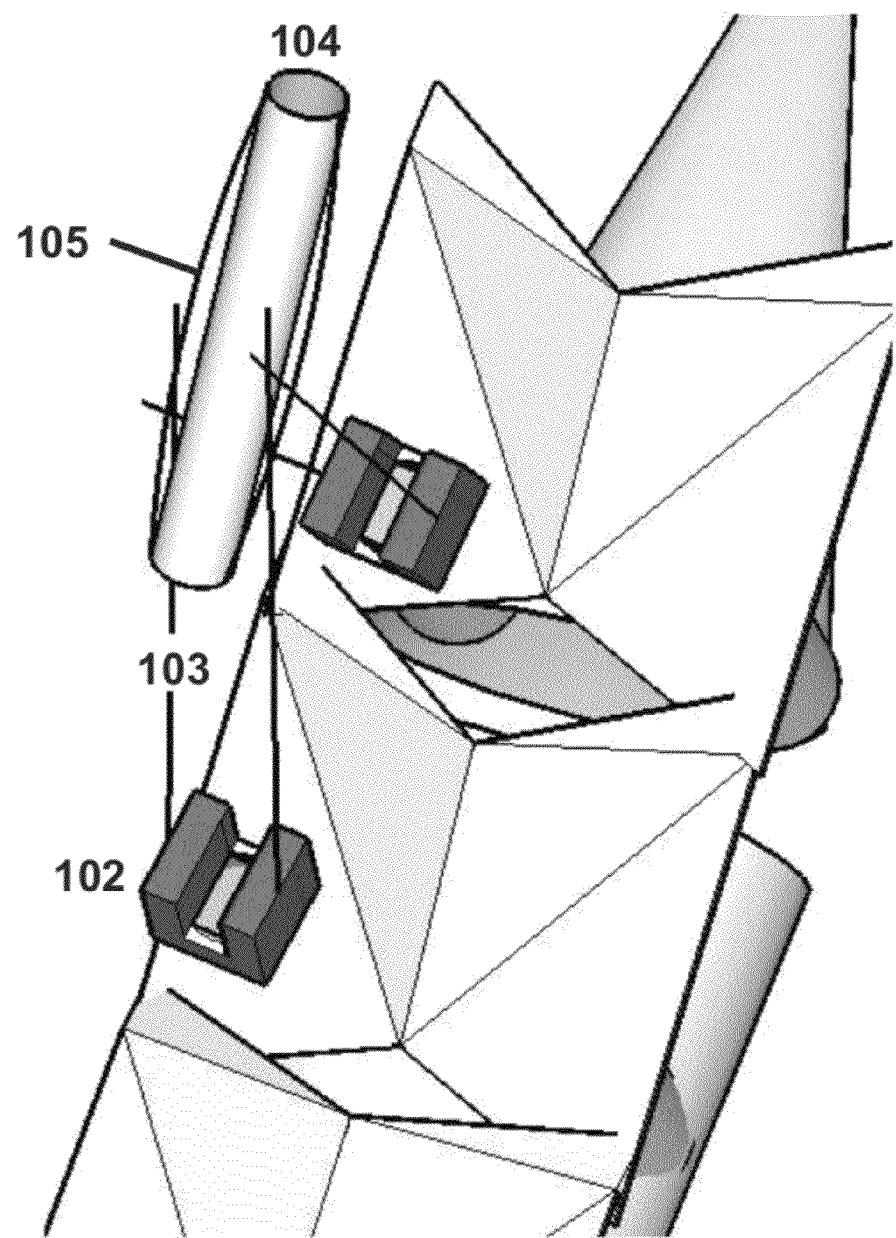
FIG. 8 shows the rod with retention threads being directed down to two screw heads (one for each longitudinal end of the rod), along screw head guide wires (corresponding to each side of each pedicle screw head) inserted through the rod retention loop on each side of the rod. The rod retention threads "trap" the guide wires so that the ends of the rod cannot be pushed out of the screw head.
Figures 12A, 12B, 12C:
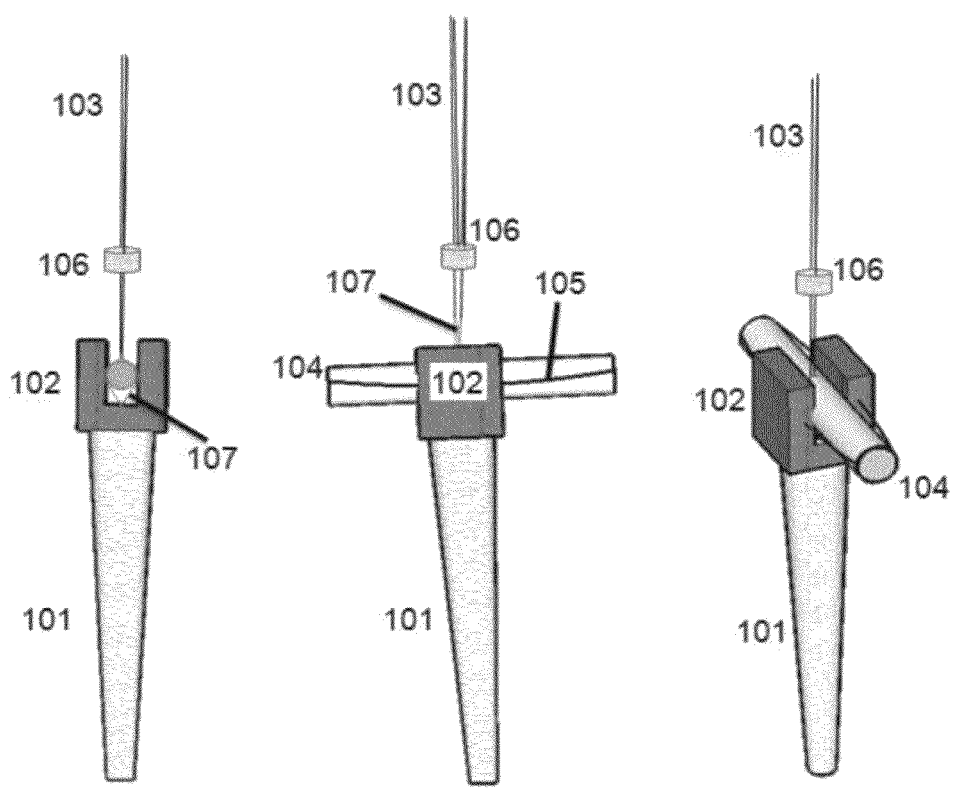
FIG. 12A-C shows how the threads, as in FIG. 11A-11F, can be wrapped around the rod and brought together to guide a cannulated locking assembly (i.e. cap) as well as other cannulated tools (not shown) down to the screw head.

In an alternative embodiment there may be a single wire 103 on only one side of each screw 101/102 or screw head 102. This embodiment further reduces the volume of stabilizing elements (screw head wires) that must fit through the minimal incision but also reduces rod stability. When only one screw head wire 103 is used per pedicle screw 101/102 it is recommended that at least one rod retention thread 105 also be used (see FIGS. 7 and 8 for illustration of the rod retention threads 105). The screw head wire 103 should be inserted through the loop formed by the rod retention thread 105 along the lateral side of the rod body 104.

In another alternative embodiment, instead of one or more wires 103, there may be one or more upwardly directed shafts that are not round (not shown) and are attached to a side of the screw head 102. The unique shape of the shaft would prevent insertion tools from turning or rotating around the shaft (i.e. during their descent to approach the screw head 102). Thus any shaft that is not cylindrical would be capable of guiding tools that have a complementary non-cylindrical shaft holder attached to the tool. For example, a shaft that has a cross section of an oval, square, rectangle, triangle, cross, trapezoid, star, or any other shape besides a circle would be able to prevent an insertion tool from rotating around the shaft as long as the insertion tool is equipped with a complementary shaped holder through which the shaft fits precisely. A single shaft guidance mechanism that is thicker than a wire would also likely be more rigid than a wire. However, as long as the screw head 102 is multi-axial, there would be some flexibility in moving the shaft around in the incision.

The screws 101 and screw heads 102 themselves may also have any one of several different vertical and horizontal cross-sections including both circular and non-circular, rectangular, square, hexagonal, etc. The screws 101 and screw heads 102 are preferably made of a titanium alloy or stainless steel.

The rods 104 are preferably cylindrical but may alternatively have a non-circular cross-section (triangular, square, hexagonal, etc.) so long as the seat of the screw head 102 is shaped correspondingly to accommodate. The rods 104 are preferably formed of polyetheretherketone (PEEK) but may also be made of any other biocompatible minimally flexible polymer or metal.

In another alternative embodiment there may be more than two wires 103 per pedicle screw 101/102. Preferably, if more than two wires per screw are used, there is at least one wire on each side of the screw with more than one wire on at least one side. An equal number of wires on each side improves stability and prevents lopsidedness. However, every patient's anatomy is slightly different and when curvature (i.e. scoliosis) and/or other aggravating conditions are present stability during rod 104 insertion may be best achieved by an asymmetric distribution of screw head wires 103 around the perimeter of a screw head 102. In any case, the spinal surgeon is in the best position to make this decision about the appropriate screw head wire 103 and rod retention thread 105 set-up to use based on the individual needs of a particular patient.

The wires 103 on any one screw 101/102 can be placed at various positions around the periphery of a screw (rather than just on the sides) for enhanced stability and control. Screw 101/102 is used to refer to the entire screw including the screw shaft 101 and the screw head 102 collectively. The wires may be uniformly distributed and symmetrical around the periphery or they may be asymmetrical and staggered. For example, having four wires on a screw head (i.e. one wire on each edge: north/top, east/right, south/bottom, west/left) ensures that the screw head 102 is oriented along the axis of the rod 104 during transport of the rod through the incision and into a first screw head. Limiting the open regions around the perimeter of a screw head 102 by effectively creating a wire cage can also force the rod 104 to turn in the right direction (or force the screw head to turn to accommodate the rod) when it moves from a vertical longitudinal to a transverse lateral orientation after placement of a first end in a first screw head while the other end is being directed for placement in a second screw head. The number of wires, their sizes (i.e. diameters and lengths), shapes, flexibility, and strength may be adjusted to suit a particular procedure in a particular patient based on the incision size to optimize screw stability and facilitate rod alignment while avoiding entanglement of too many wires. Contemplated embodiments include those with from 1 to 10 wires per screw/screw head, especially those with 2 to 4 wires.

Instead of multiple long wires connected to the screw head 102 on each side, a single long wire 103 (or thread) is connected to several short wires 111 which in turn are connected to each side of the screw head. Thus, multiple wires 111 are still connected to each screw head 102 but these multiple wires are also connected to one another in an area above the screw head to form single wire 103 extending through the incision. These multiple short wires 111 may still function to bound or limit the movement of a rod 104 at least at the base of the screw head 102. The short wires 111 give the advantage of creating a wire cage by which the rod 104 is forced to sit down into the seat of the screw head 102. The long single wire (or thread) 103 reduces clutter and confusion at the skin incision that occurs when too many wires are present. The multitude of short wires 111 distributed away from the longitudinal entry axis into approximately the same axis along which the rod 104 will ultimately lay also allows the long wire 103 and accompanying instruments to adjust the orientation and angle of the screw head 102 in this axis (the rod axis, approximately perpendicular to the longitudinal entry axis used during rod insertion). The screw head 102 is configured to form a concave channel in which the rod 104 will eventually come to sit/rest. The concave channel may be U-shaped when a vertical cross-section is taken but any substantially concave shape suited to retain a rod 104 and with dimensions corresponding to those of the rod 104 will work. The upper edges of the screw head 102 itself or those of another intermediate element 110/112/113 to which it is attached, are configured to receive an incoming rod at a wide range of angles and smoothly direct it into the proper angular configuration to fit into the screw seat.

As an alternative to the screws 101 or the screw heads 102 being attached directly to upwardly directed guide wires 103 or guide shafts, there may be an intermediary flange, flanged leaflet, sheet 110, extensor/extended tab 112, a mechanical clamp/device 113, or other element in between the two. The screw 101/102 or screw head 102 at its outer edges may transform into (integral therewith) or attach to a separate element that is directly attached to the guidance wire/shaft 103 such that the screw 101/102 or screw head 102 and the guidance element 103 are indirectly connected. The intermediate element is preferably specially adapted to readily detach from the screw 101/102 or screw head 102 when desirable, such as after securing the rod 104 in proper position and locking it in place. Detachment may be through a snap-off/pop-off mechanical mechanism that might be activated through a push-button at the proximal end of a surgeon's tool; through tearing along a perforation; through cutting, twisting, wagging, burning, heating, radiating, ultrasonically vibrating, electrifying/electrocuting, dissolving, unscrewing, or any other means. In this case with the guidance wires or upward shafts 103 attached directly to the intermediate and readily detachable element 110/112/113 the guidance wires 103 themselves may be more securely fastened to the intermediate element 110/112/113. For example, the wires 103 might be soldered or welded to an extensor tab 112 that snaps into/onto and snaps out of/off of a groove or protrusion on the screw head 102. At least a portion of the extensor tab 112 may be threaded to mate with a screw 101/102 or screw shaft 101 having corresponding threads or to align a rod 104 having some corresponding threads.

The intermediate element may be in the form of a sheet 110 of a very thin material that is both flexible and can be tensed by pulling or tightening. When pulled tight the sheet 110 functions to guide the rod 104 into the seat of the screw head 102. Such material may be rubber.

An intermediate element may be an inwardly tapered flange 110 attached to an inner top edge of the screw head 102 and placed symmetrically about the screw seat in which the rod 104 sits. Such a flange 110 is configured to allow a malaligned rod 104 or screw head 102 to rotate and adjust relative to one another as the rod is inserted into the seat of the screw head until the two are acceptably aligned. The inwardly tapered sides of the flange 110 may take the form of convexly curved wings 110 that form a channel for the rod 104 between them.

Alternatively, the intermediate element may be an extensor tab 112 with straight rather than convex sides. Preferably, the tab is triangular which may be formed by removing the corners of an otherwise rectangular tab. The wider base of the triangle may attach to the screw head 102 as shown in FIG. 18A-18C.

The function of the screw head 102 or intermediate element 110/112/113 is to create a channel into which a rod 104 can be easily guided by the upwardly directed guide wire 103/guide shaft. The screw head or intermediate element is adapted to accept a large degree of malalignment of the rod and the screw seat relative to one another and then guide the rod into the screw seat until substantially perfect alignment is achieved. The advantage of this is that the system does not require starting over, pulling out, and reinserting the rod when it turns out the initial positioning is not ideal.

The wires, threads, and intermediate elements described herein may be attached to the screw or screw head on the outside, on the inside, or through a cannulated portion of the downwardly directed screw shaft 101. Many attachment locations are possible so long as it does not interfere with the ability of the screw shaft 101 to be drilled into the pedicle and the ability of the rod 104 and locking assembly 106 to be received into the seat of the screw head 102.

The wire, thread, or upwardly directed shaft 103 may be attached to the downwardly directed screw shaft 101, the screw head 102, or an intermediate element (i.e. flange, sheet 110, extensor/extended tab 112) with glue, soldering, thread, sutures, string, a mechanical clamp 113, etc.

In embodiments in which a mechanical clamp 113 is used to connect the upwardly directed guidance element 103 to the screw head 102, the clamp 113 preferably has 2 leaves that are connected under the head 102 or at least below where the rod 104 comes down so as not to impede the path of the rod. After closing the locking assemblies 106 to secure the rod 104 in place within the screw head 102, the clamps 113 can be removed. Removing the clamps 113 from the screw head 102 also removes the wires 103 attached to the clamps 113. The clamps 113 may be removed by any means feasible in the limited space including (but not limited to): (i) by breaking the connection (like detaching the extended tabs 112), (ii) by cutting a material that holds the 2 leaves together, (iii) unclamping or unbuckling, and (iv) unvelcro-ing.

Alternatively, in some embodiments the locking assembly may be part of the clamp 113 such that the clamp is not removed but remains to hold the rod 104 (see FIG. 19A-19C). In such situations, the guidance wires 103 only are simply detached from the clamp-locking assembly combination unit.

Instead of a mechanical clamp with moving parts, the intermediate element (between screw head 102 and wires 103) may also simply be a metal or plastic device that has no moving parts but traps the head 102 securely into it. The intermediate metal or plastic device can be removed by means including (i) snapping a thin center part connecting 2 halves of the device, or (ii) cutting a string that connects 2 parts of the device. If the locking assembly 106 for the rod 104 is distinct from the intermediate metal or plastic device, then the device can be removed along with the wires after the rod is placed. If the locking assembly is integrated with or dependent upon the intermediate metal/plastic device, then the device should stay in place after the wires 103/111 only are detached from it.

In another embodiment illustrated in FIG. 11A-11F, the wire 103 or an extension thread 107 thereon, can be attached to the area within the screw head 102 where the rod 104 would eventually sit, such as at the base of the screw head and/or to the upper end of the downwardly directed screw shaft 101. For example, the wire 103 or its extension 107 may be attached within the cannulated portion of a cannulated screw. By using flexible wire or extension thread 107, the wire/thread can wrap around the rod 104 as the rod is seated into the screw head 102. The wire/thread can then be threaded through cannulated tools and a cannulated locking assembly 106 above the rod.

Optionally, color-coded wires 103 and/or screws 101 may be provided to assist doctors, technicians, and medical personnel in identifying elements, performing the procedure, and monitoring progress during follow-up visits. Alternatively, some other form of visual coding, such as with particular materials and/or only visible under certain conditions may be used to distinguish wires, screws, and other elements (i.e. fluorescent markers, radioactive isotopes, radioopaque markers visible on X-rays, magnetic nanoparticles, etc.). Another alternative or complementary coding means can be sensed by touch (different surface textures) or sound (tactile or auditory) rather than or in addition to visually. The coding could be correlated with right and left sides of the body, medial vs. lateral elements, wire/screw sizes, wire/screw shapes, wire flexibility, and/or wire strengths, among other possibilities. This list of variables with which a coding or tagging system may correspond is intended to be illustrative rather than exhaustive. One preferred coding system provides markers or color coding for wires that are intended for the medial side of the rod versus those intended for the lateral side of the rod. This coding would allow for easy separation of the wires 103 when the rod 104 is inserted. This coding would also help the insertion of tools and the locking assembly 106 along the medial side and lateral side wires 103. Some elements (wires 103, screws 101, screw heads 102, rods 104, retention threads 105, locking assemblies 106, etc.) with similar characteristics may be coded in groups such as all medial side wires being red while all lateral side wires are green.

Any locking assembly 106 can be used with the present invention. The precise design of the locking assembly 106 is not important so long as it is configured to retain the rod 104 within the screw head 102 for a secure and lasting stabilization. Examples of locking assemblies 106 that might be employed include screw-on nuts, press-on caps, fast-drying glue, a tiny swinging gate or door with a latch, a series of elements that can be deployed to tighten around the periphery of the rod, etc.

Since a rod connects two or more separate vertebrae, the rod can first be secured into position (locked or tightened) though the locking assembly on a first vertebra and then subsequently on a second vertebra. In some cases after the rod is firmly secured to the screw on the first vertebra, the relative positioning of the vertebrae can be adjusted by the surgeon by moving the vertebrae closer together or farther apart before the rod is secured to the screw on the second vertebra. With only one side of the rod locked into place the other side of the rod can easily be adjusted in position. For example, the rod can vertically slide forward or backward through the locking assembly until the desired distance spanned by the rod between locking assemblies is obtained.

The wires 103 can be attached to the screw heads 102 by a number of mechanisms. The retention threads 105 can be attached to the ends of the rods 104 by the same assortment of mechanisms. The simplest attachment mechanism is to solder or glue the wire/thread to the screw head/rod. The solder or glue can then be cut or broken off later. Neither the lateral retention threads 105 on the rod 104 nor the upwardly directed guidance wires 103 on the screw 101/102, or on the screw head 102, are needed after the rod 104 has been securely placed within the screw head 102.

The retention threads 105 on the rod 104 that hold it close to the guide wires 103 as it is guided into position are preferably made of a flexible material including metal wire, nitinol, rubber, suture, plastic, polymer, and biodegradable material. The retention thread 105 should be easily removable after the rod 104 has been secured in an aligned position in the seat of the screw head 102 and locked in.

Alternatively, the wire/thread could be threaded into a threaded connector in the side of the screw head/rod so that the wire/thread is unscrewed at the end of the case.

Other embodiments include attaching the wire 103/retention thread 105 by dissolvable sutures tied to the screw head 102/rod 104 and to the end of the wire/retention thread with a small loop or grooves in the screw head/rod. Suitable dissolvable suture materials include biocompatible synthetic absorbable materials such as those made primarily of polyglycolic acid (PGA) or other proven compositions. Specific brands of materials include Vicryl™ (from Ethicon), Biovek™ (from Dynek), Visorb™ (from CP Medical), Polysorb™ (from Covidien's Syneture), and Dexon™ (also from Covidien's Syneture). The materials can be tailored to degrade or absorb in an amount of time that corresponds with sufficient internal healing to successfully hold the fusion. For example, standard Vicryl™ typically maintains tensile strength for three to four weeks. The materials may also be impregnated with drugs or biomolecules (i.e. triclosan) to accelerate the healing process and prevent infection. When the biodegradation (i.e. bioabsorption, bioerosion, etc.) time for the suture material is too long and the sutures are unnecessary immediately following the procedure the sutures can instead be promptly cut or burned at the end to disconnect the wire/retention thread from the screw head/rod.

Yet another option for the "wire to screw head" or "retention thread to rod" attachment mechanism is to secure using a material that burns, breaks, or dissolves upon the application of current (i.e. radiofrequency current). This option permits the connection to be easily broken by simply passing current through the wire or thread. Preferably, the wire/retention thread breaks down in response to current applied outside the skin. Alternatively, an insulated guide wire can be used to apply current internally in a targeted and minimally invasive manner. An insulated guide wire would allow the current to pass directly from an external tip (outside the body) to the current-sensitive material at an interior tip near the pedicle screw.

In still another preferred embodiment for attachment, the selected material (i.e. elastic string or rubber) is both flexible and can be tensed by pulling or tightening. The key is to use very thin material that can be both flexible and become tense. These dual properties allow the material to reliably guide the rod and tools down through the small incision without breaking while adapting to share the limited space. Unless it is also biodegradable the flexible, tensile material of string/rubber will need to be cut/broken/burned off or untied from the screw head and wire (or rod and retention thread) at the end of the procedure.

Instead of using an intermediary material to connect the wire to the screw head and/or to connect the retention thread to the rod, another possibility is for the wire and/or retention thread to be formed of the same materials as the intermediary connectors described above. In this situation, it is the wire or retention thread that is itself burned or cut at the end of the procedure.

The final result in all cases is a clean, successful pedicle screw fusion just like that which results from screws and rods used in an open procedure but with a smaller incision and fewer components.

The material through which the rod-guiding wire is attached to the screw head may be the same material of which the wire itself is derived or a separate material. The wires themselves are preferably formed of a biocompatible metal having both strength and durability. In a preferred embodiment, the wires are formed of nitinol (nickel titanium alloy).

The material through which the retention threads 105 of the rod 104 are attached to the ends of the rod may be the same material of which the retention threads themselves are derived or a separate material. The retention threads are preferably formed of a biocompatible metal having both strength and durability. In a preferred embodiment, the retention threads are formed of nitinol (nickel titanium alloy). Alternatively, another preferred embodiment is for the retention threads of the rod to be made from a biodegradable thread so that it does not have to be removed after placement. Another advantage of thread is that it would not interfere with the rod and cap locking mechanism 106 if it were caught in between the cap 106 and screw head 102 threads.

To complement the wire guides 103, the present invention also provides a special rod 104, with its own retention threads 105, that can fit between the wires. By attaching a small loop or ring at the ends of the rod, two threads can be tied though the loops with good tension along the sides of the rod. This way the wires 103 will pass in between the rod 104 and the thread 105 to prevent the rod from slipping out and around the most superior or inferior wires. (See FIGS. 7 and 8.) The retention thread 105 may also be attached to the rod by means other than loops or rings at its ends. The rod 104 may have holes or piercings therein for securing the thread to it. The rod may have grooves at its ends with which the thread engages. The thread 105 may be glued on near the ends of the rod. Rod retention threads 105 restrain the rod 104 to riding the wires 103 and eliminate the risk of internal rod displacement away from the target screw site 102. The retention threads 105 also expedite rod 104 placement into the screws 102/101 to decrease total procedure time.

The retention thread 105 may take the form a strip or long sheet of material rather than an ordinary thread. The retention thread material should be flexible, strong, and biocompatible.

Figure 2:
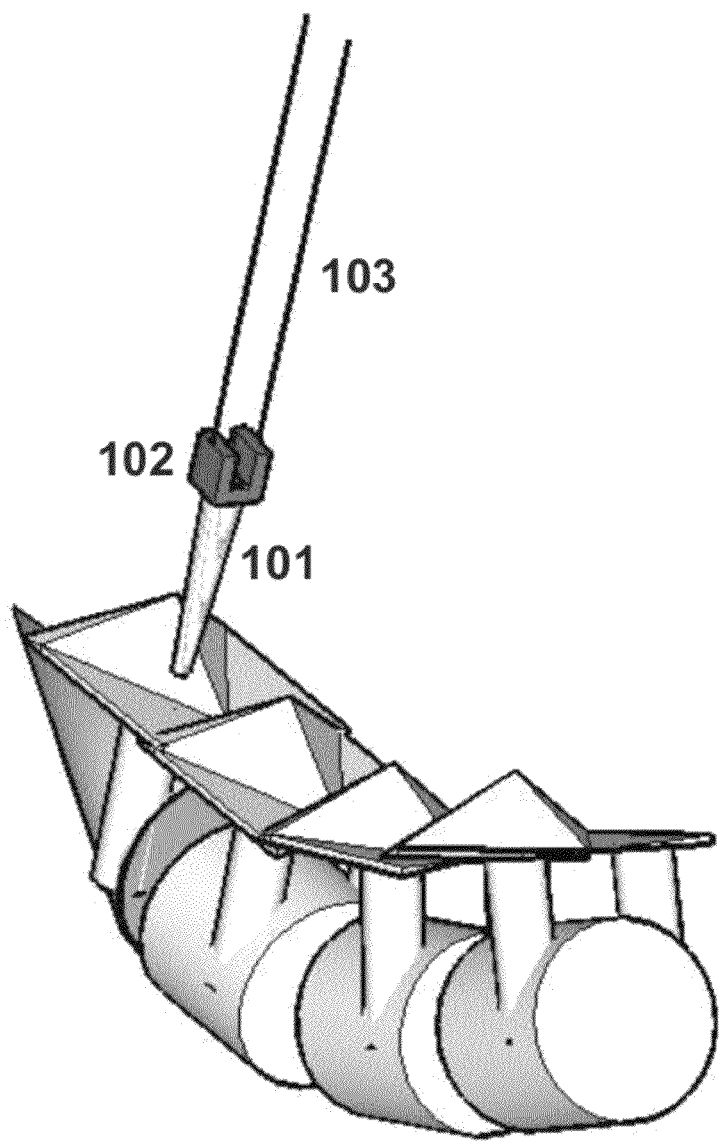
FIG. 2 shows the pedicle screw being inserted into the pedicle portion of a vertebra on the anatomical right side of the central lamina.
Figure 3:
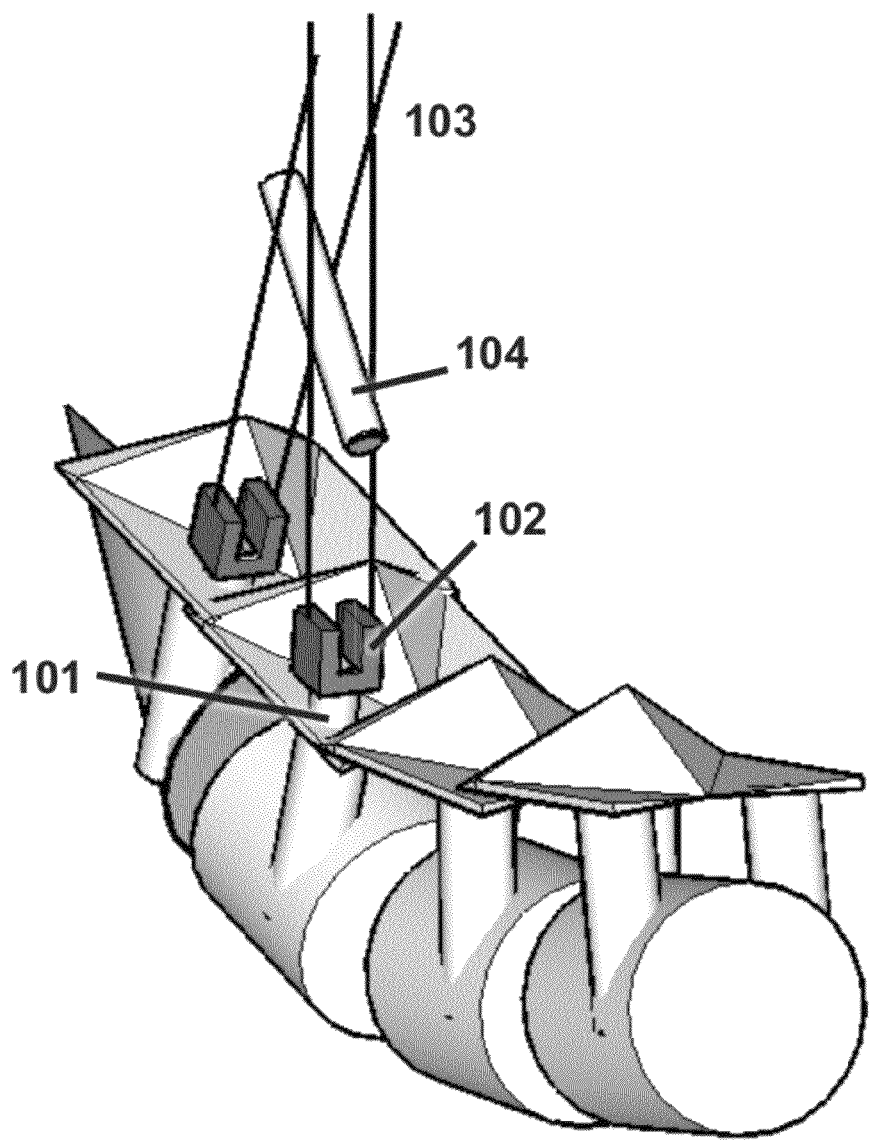
FIG. 3 shows two pedicle screws in position on two adjacent vertebrae on one side of a vertebral column, with the screw shafts buried within the vertebral bones and the U-shaped screw heads protruding from the pedicles' surfaces. Also shown is a rod being guided down (at an angle) to the screw heads, between each of two sets of two wires, one for each screw.
Figure 4:
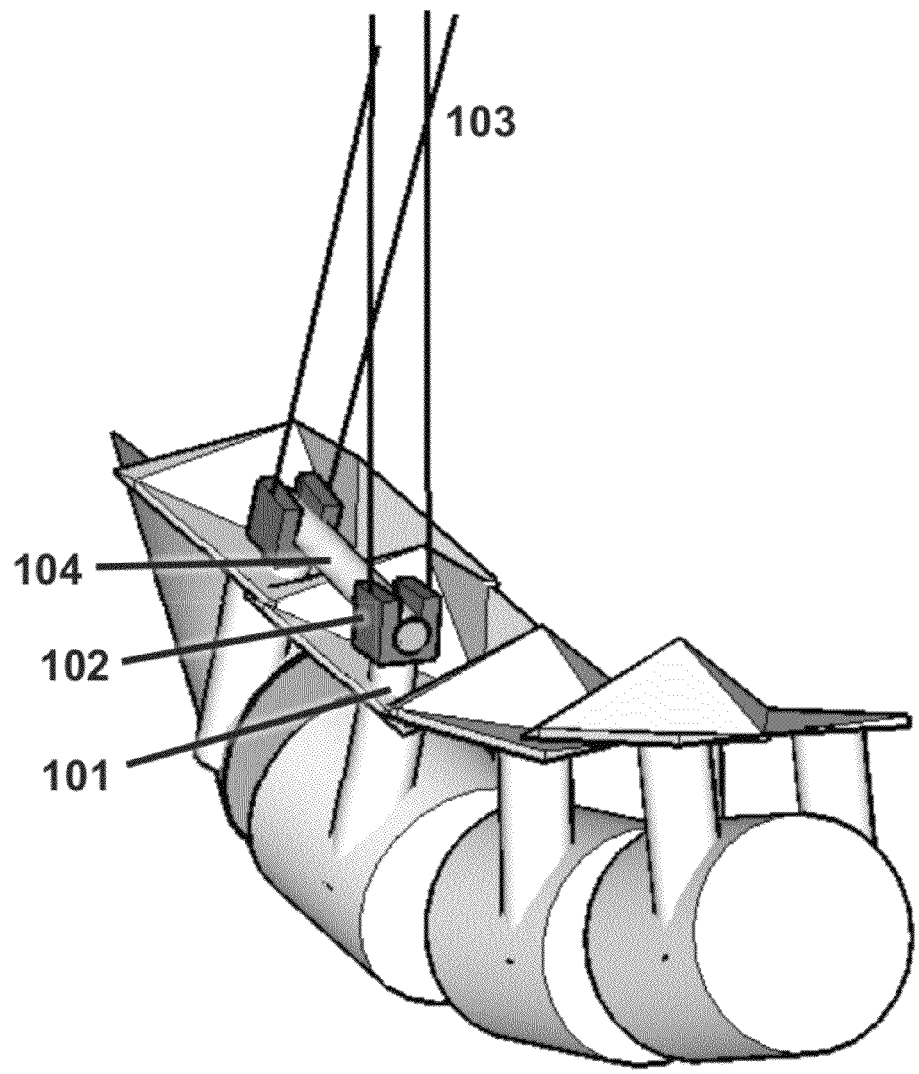
FIG. 4 shows the rod in a proper final position fully inserted within the screw heads of the pedicle screws in adjacent vertebrae along one side of a vertebral column for a partial (half-finished, the other side having yet to be stabilized) one-level stabilization. The locking assemblies are not shown here but may also be guided by the wires down to the screw heads.

The steps for the placement of the pedicle screws and rods for a "Micro open" approach are as follows. First, using fluoroscopy or stereotactic guidance, a single small skin incision 1-4 cm lateral to a midline that will accommodate all pedicle screws is localized. Next, using either a percutaneous Jamshedi/Kirschner-wire (K-wire) approach, a Wiltse muscle splitting approach, or tube system, the pedicle screws are placed (see FIG. 2). The pedicle screw inserter has loop attachments that hold the side wires of the pedicle screw during placement. After each pedicle screw is placed, the side wires are pushed to the side of the incision to make room so that the other screws can be placed without entanglement. After all screws are placed, a screw head turner is inserted and guided down to the screw heads along each pair of guide wires to align the heads of the screws in preparation for receiving the rods (see aligned screw heads in FIG. 3).

Figure 5:
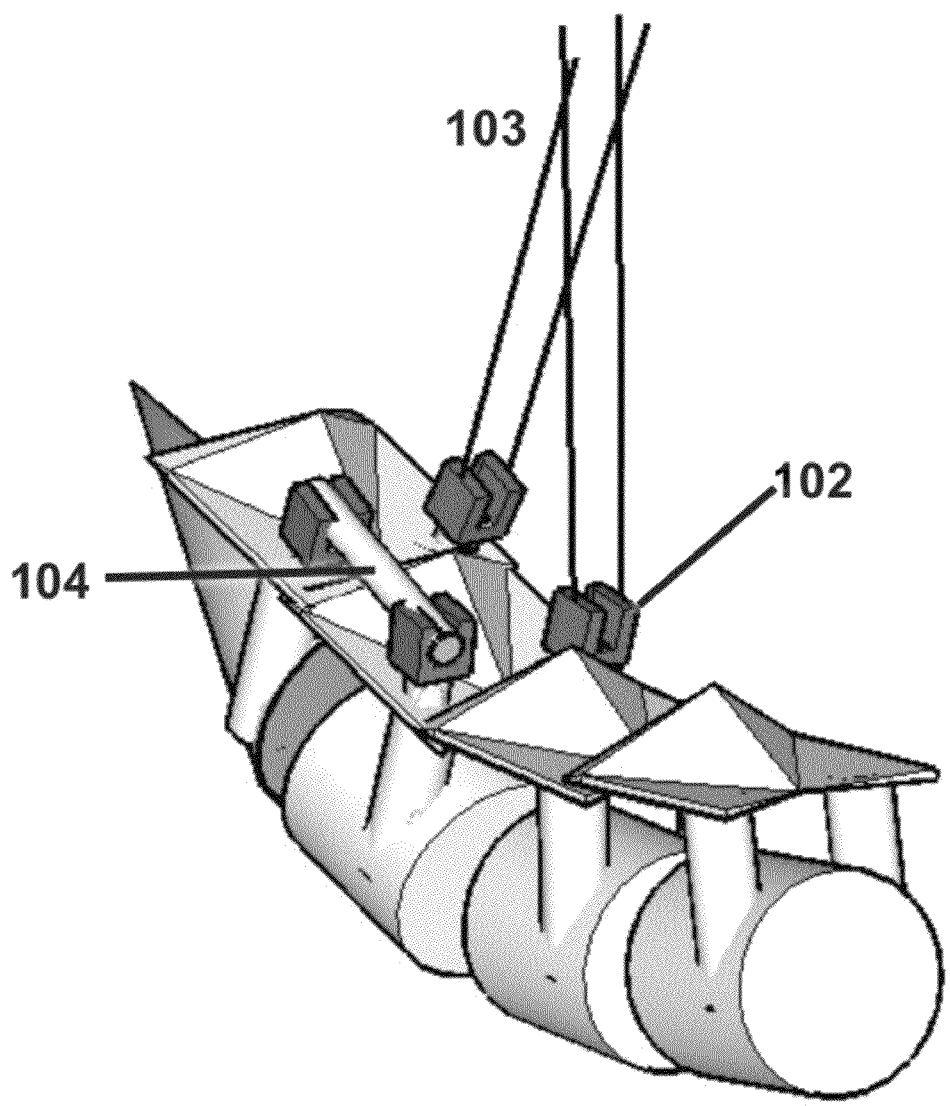
FIG. 5 shows the wires (for guiding the rods, locking assemblies, etc.) having been detached from the screw heads of the pedicle screws along the anatomical right side of the vertebral column, but with the same screw head-wire system still in place on the anatomical left side of the vertebral column ready to accept and guide a rod down to the pedicle screws. The locking assemblies are not shown.
Figure 6:
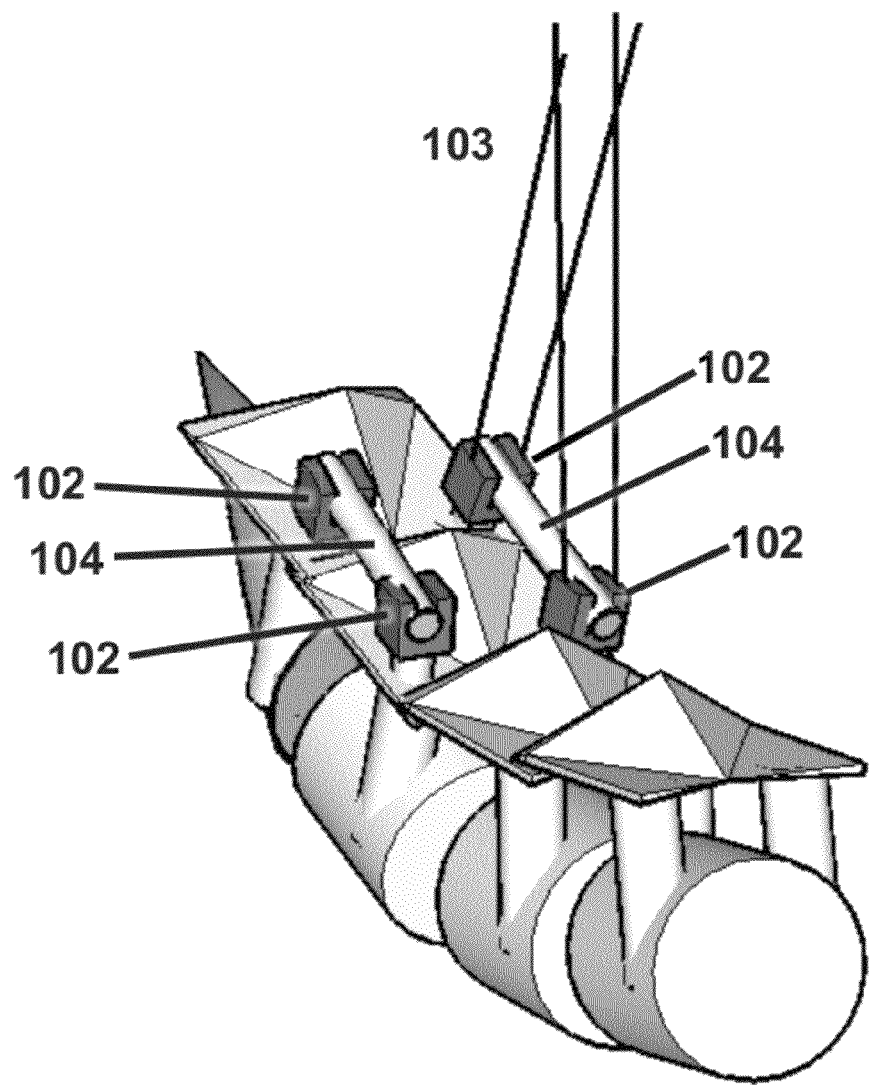
FIG. 6 shows the second rod in place within the screw heads on the anatomical left side pedicles of the vertebral column, with the detachable screw head wires remaining on only the anatomical left side.

With the screw heads aligned, the side wires are split between the medial and lateral sides. Then a rod is slid in between the medial and lateral wires into the screw heads. Preferably, the rod should be bent before insertion. Markers on the guide wires at predefined distances from the tip of the guide wires can help guide the surgeon in bending the rod to the correct curvature. Guide wires coming out of a single incision are similar to light rays that have been focused by a convex lens. These light rays converge at a point and then create a mirror virtual image on the other side of the focal point. This same concept can be used to create a mirror image of the curvature of the rod to guide the bending of the rod to accurately fit into the screw heads. (See FIGS. 4 and 15A-15C). After each end of the rod is properly positioned within a screw head, locking nuts or caps are screwed on the screw heads to secure it in place. Alternatively, a compressor that is guided by the wires is used to compress pedicle screws on adjacent levels and then final tightening can be done during compression. The screw head guide wires are then removed by any means including cutting, twisting, wagging, burning, radiating, dissolving, unscrewing, etc. (see FIG. 5 and FIG. 6, left side). Once the screws and rods in all vertebrae to-be-fused along one side of the vertebral column are stabilized, their mirror-image counterparts should be placed along the opposite side of the same vertebrae using similar fluoroscopic localization or other imaging means (see FIG. 5 with one rod, preparing for the second, and FIG. 6 with two rods placed).

The present invention can be used to dynamically stabilize or fuse vertebrae while at the same time removing a defective intervertebral disc and inserting a spacer in its place. The spacer may include bone graft material or bone inducing material incorporated therein to encourage healing. Exemplary bone inducing materials include bone morphogenetic protein, tricalcium phosphate, hydroxyapatite, and collagen.

The various elements (wires, screws, screw heads, rods, retention threads, locking assemblies, etc.) of the present invention may be provided in a range of sizes, shapes, strengths, flexibilities, and other physical characteristics to best accommodate individual patients and particular applications.

Figure 13C:
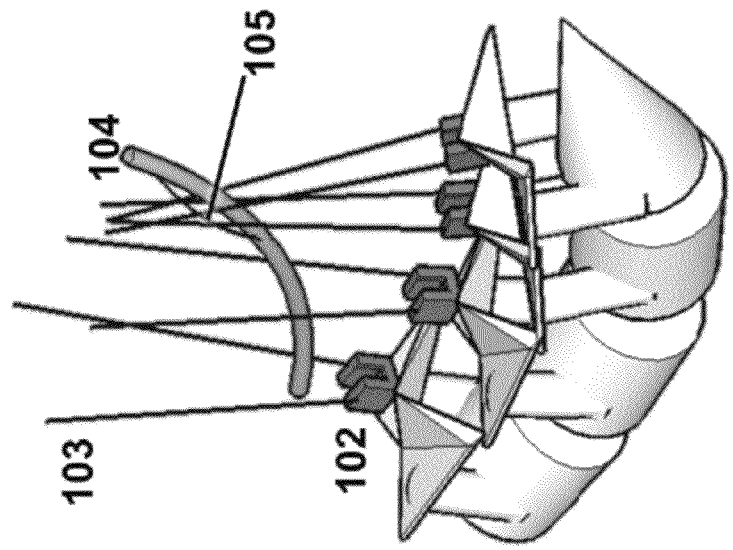
FIG. 13A-13C shows the insertion of a longer rod through 4 sets of guide wires attached to 4 pedicle screws in a three level stabilization.
Figure 13B:
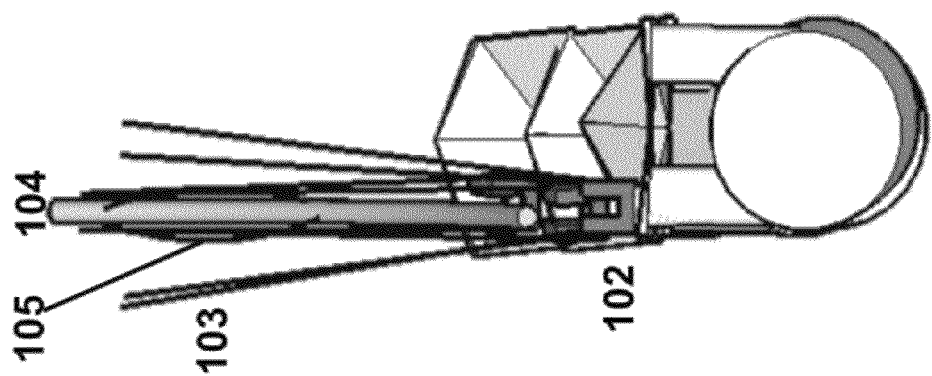
Figure 13A:
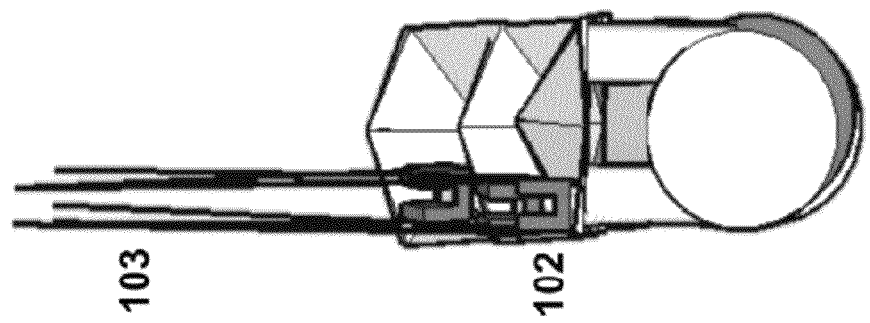

FIG. 13A-13C shows how for a three level stabilization the rod can be guided down by the wires on a first screw head while the wires on a second and third screw head are splayed outward or bent to open the encatchment area for the rod to easily enter. In the conventional case of pedicle screw towers, the rod had to be precisely inserted through the small opening within each rigid tower. The present invention overcomes this difficulty.

Figures 14A, 14B, 14C:
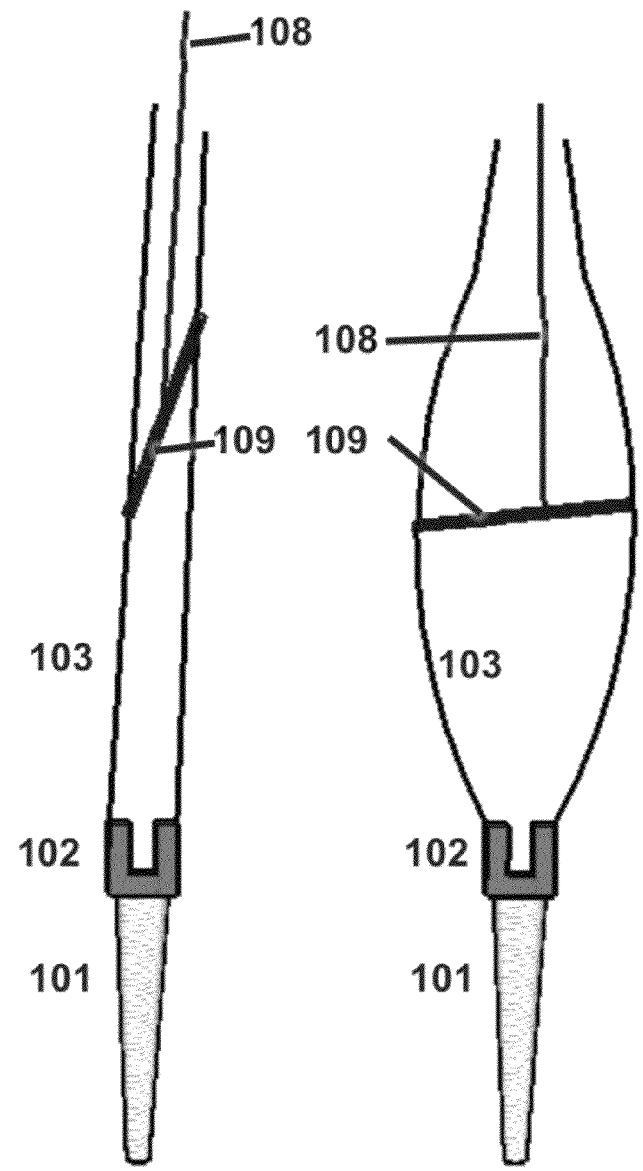
FIG. 14A-14C shows a preferred embodiment using a tool to separate the guide wires deep below the skin surface. In this manner, the skin incision remains small. A "T"-shaped tool with a hinged "T" portion is attached to the guide wires and slid partially down towards the screw head. As the hinged "T" is opened, the middle section of the guide wires is separated. This opened window allows the rod to be tunneled in between the guide wires, especially in instances where the rod and pedicle screw heads are inserted through separate incisions, as shown in FIG. 13A-13C and FIG. 15A-15C.
Figure 16D:
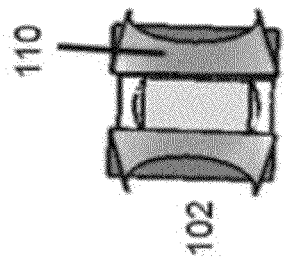
FIG. 16A-16D shows a preferred embodiment of flanged attachments that help the rod to find the proper orientation to best fit into the screw head. As shown, each attachment is preferably convex in a direction towards the rod so that as the rod approaches the screw head, the entrance to the screw head can accept a large range of angles in which the rod is oriented and still receive the rod, gradually improving the rod's orientation as it gets closer to the seat of the screw head.
Figure 16C:
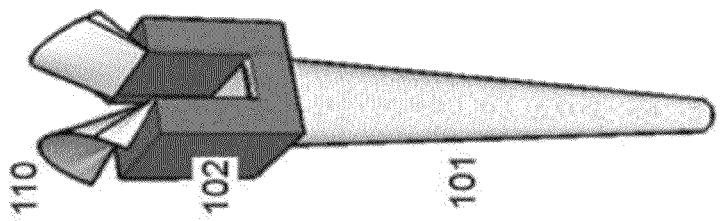
Figure 16B:
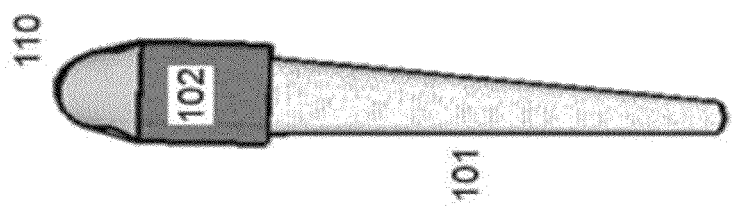
Figure 16A:
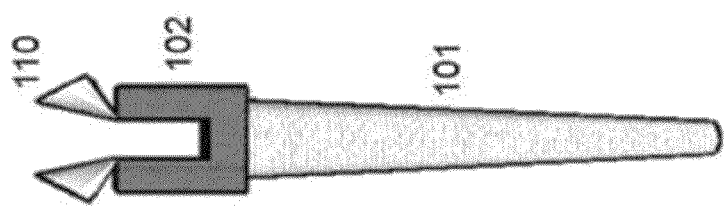

As shown in FIG. 14A-14C a refined T-shape tool 108/109 may be used to separate the wires 103. This gesture prevents them from becoming tangled (or disentangles them) and opens the space in between them such that a rod can be passed through it to enter the screw head. The horizontal arms 109 of the "T" extend outward perpendicular to the longitudinal insertion axis 108. These arms 109 may be aligned parallel against the main longitudinal body during insertion and removal. They may also be inside the main body and deployed from within via telescopic extension or a spring-like mechanism. The end of each horizontal arm 109 may be U-shaped, V-shaped, or circular such that a wire 103 can be retained within it. If the ends are U-shaped or V-shaped the T-shaped tool 108/109 can be disconnected from the wire 103 easily after spacing by collapsing the arms to realign against the longitudinal insertion axis 108 or to collapse into the main body. If the ends are a closed loop shape such that the wires 103 are fed through them and trapped within them, the loops should be configured to open to release them (like a jewelry clasp) after the tool 108/109 has performed its function.

The present invention is not limited to the embodiments described above. Various changes and modifications can, of course, be made, without departing from the scope and spirit of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A system for bone stabilization comprising:
   a first screw having a first screw head comprising opposing sides;
   a second screw having a second screw head comprising opposing sides;
   a spinal fixation element configured to be retained in at least one of the first screw head and the second screw head between the opposing sides;
   at least a first guiding element extending away from the first screw and configured to extend through a skin opening through which the first guiding element is delivered, wherein the first guiding element comprises at least one elongated member extending away from each of the opposing sides of the first screw head; and at least a second guiding element extending away from the second screw and configured to extend through the skin opening, wherein the second guiding element comprises at least one elongated member extending away from each of the opposing sides of the second screw head;

wherein at least one of the elongated members is flexible in at least a plane substantially parallel with the opposing sides of the screw head from which said at least one elongated member extends;

wherein the first guiding element and the second guiding element are configured to overlap, and wherein the first guiding element and second guiding element are capable in their overlapping configuration of guiding the spinal fixation element towards contact with the first and second screw heads at any angle permitted geometrically by the guiding elements including an angle not parallel with a long axis of either of the guiding elements.

2. The system of claim 1, wherein the first screw, the second screw, the spinal fixation element and the first and second guiding elements are configured to be delivered through the same percutaneous or minimally invasive skin incision, wherein the size of the skin incision is smaller than the sum of the smallest cross sectional sizes of the first and second screws.

3. The system of claim 1, wherein the first guiding element comprises at least one wire connected to the first screw head and/or the second guiding element comprises at least one wire connected to the second screw head.

4. The system of claim 3, wherein the first guiding element comprises at least one wire portion connected to each side of the first screw head and the second guiding element comprises at least one wire portion connected to each side of the second screw head.

5. The system of claim 3, wherein the wires are connected to the screw heads with extended tabs attached to the screw heads that are configured to be easily detached from the screw heads.

6. The system of claim 1, wherein the first and second guiding elements are attached to the first and second screws, respectively, through a mechanical clamp or device that securely holds the respective screw heads, and the clamp or device is removable along with the guiding elements after the spinal fixation element is guided into contact with the first and second screw heads.

7. The system of claim 1, wherein at least one of the first and second guiding elements comprises a rigid tower.

8. The system of claim 7, wherein both of the first and second guiding elements comprise rigid towers.

9. The system of claim 1, wherein one or both of first and second guiding elements comprises a short tower and at least one wire, wherein the short tower is configured to be positioned below the skin opening and the at least one wire extends through the skin opening when the associated screw is delivered into bone.

10. The system of claim 1, wherein the spinal fixation element is a cylindrical rod.

11. The system of claim 1, wherein one or both of the first and second guiding elements comprises one or more long wires attached to multiple short wires connected to the associated screw head.

12. The system of claim 1, further comprising a locking assembly configured to lock the spinal fixation element to the first and second screw heads.

13. The system of claim 12, wherein the locking assembly is built in or part of the first and second screw heads.

14. The system of claim 1, wherein the guiding elements are configured to intersect at an intersection point, and further comprising means for measuring the depths of each guiding element below the intersection point and to reflect the measured depths above the intersection point to produce a virtual reflected image of the relative positions of the screws so that the length and contour of the spinal fixation element can be pre-bent or chosen by a surgeon to the correct curvature and size.

15. A system for bone stabilization comprising:
a first screw having a first screw head;
a second screw having a second screw head;
at least a first guiding element extending away from the first screw head and configured to extend through a skin opening through which the first guiding element is delivered;
at least a second guiding element extending away from the second screw and configured to extend through a skin opening through which the second guiding element is delivered; and
a spinal fixation element configured to be retained in both the first screw head and the second screw head, the spinal fixation element comprising a retention element configured to be guided by at least one of the guiding elements to assist in delivering the spinal fixation element to the first screw head and the second screw head;
wherein the retention element is attached to a region near an end of the spinal fixation element and is extendible through or along the guiding elements to raise, lower, push, pull, and rotate the spinal fixation element into position within the heads of the screws.

16. The system of claim 15, further comprising a leading thread or wire used for delivering the spinal fixation element through either a separate percutaneous pendulum approach or through the same skin incision in which the screws are placed.

17. A system for bone stabilization, comprising:
a first screw having a first screw head comprising opposing sides defining a seat between the opposing sides;
a second screw having a second screw head;
a spinal fixation element configured to be retained in at least the seat of the first screw head; and
a guiding element comprising one or more elongated members extending away at least from the first screw, the guiding element configured to guide the spinal fixation element into contact with the first screw head;
wherein at least one of the elongated members is flexible in at least a plane substantially parallel with the opposing sides of the first screw head.

18. The system of claim 17, wherein the guiding element comprises a first wire portion extending from one side of the first screw head and a second wire portion extending from a second side of the first screw head, the first and second wire portions configured to guide the spinal fixation element therebetween into contact with the first screw head.

19. The system of claim 17, further comprising one or more elongated members extending away from the second screw.

20. The system of claim 17, wherein the one or more elongated members are secured to an intermediate element detachable from the first screw.

21. The system of claim 17, wherein the guiding element comprises a tower attached to the first screw and one or more wires extending away from the tower.

22. The system of claim 17, further comprising a tower attached to and extending away from the second screw.

23. The system of claim 17, wherein the spinal fixation element is a rod having a circular cross-section.

24. The system of claim 17, wherein the spinal fixation element further comprises a retention element for assisting in delivery of the spinal fixation element over the one or more elongated members.

25. The system of claim 17, further comprising a locking assembly configured to lock the spinal fixation element in the seats of the first and second screw heads.

26. The system of claim 17, wherein the one or more elongated members are connected to flexible strands connected to the first screw and configured to wrap around the spinal fixation element.

27. A screw for use in bone stabilization, comprising:
a screw shaft;
a screw head having opposing sides to define a seat defining a channel for receiving a spinal fixation element;
at least one elongated member extending from at least one of the opposing sides of the screw head configured to guide the spinal fixation element into the channel of the seat of the screw head;
wherein at least one of the elongated members is flexible in at least a plane substantially parallel with the opposing sides of the screw head.

28. The screw of claim 27, comprising a first elongated member extending from one side of the screw head and a second elongated member extending from the other side of the screw head, wherein both of the elongated members are flexible in at least a plane substantially parallel with the opposing sides of the screw head.

29. The screw of claim 27, comprising a tower attached to the screw head, wherein the at least one elongated member is attached to the tower.

30. The screw of claim 27, further comprising a locking assembly configured to lock the spinal fixation element in the channel.

* * * * *